US008642298B2

(12) United States Patent
Van Der Werf et al.

(10) Patent No.: US 8,642,298 B2
(45) Date of Patent: *Feb. 4, 2014

(54) PRODUCTION OF ITACONIC ACID

(75) Inventors: Maria Johanna Van Der Werf, Tuil (NL); Peter Jan Punt, Houten (NL)

(73) Assignee: Nederlandse Organisatie Voor Toegepast—Natuurwetenschappelijk Onderzoek Tno, Delft (NL)

( * ) Notice: Subject to any disclaimer, the term of this patent is extended or adjusted under 35 U.S.C. 154(b) by 347 days.

This patent is subject to a terminal disclaimer.

(21) Appl. No.: 12/920,461

(22) PCT Filed: Mar. 4, 2009

(86) PCT No.: PCT/NL2009/050099
§ 371 (c)(1),
(2), (4) Date: Nov. 29, 2010

(87) PCT Pub. No.: WO2009/110796
PCT Pub. Date: Sep. 11, 2009

(65) Prior Publication Data
US 2011/0070616 A1  Mar. 24, 2011

(30) Foreign Application Priority Data

Mar. 5, 2008 (EP) .................................. 08152332

(51) Int. Cl.
*C12P 7/44* (2006.01)
*C12N 15/31* (2006.01)

(52) U.S. Cl.
USPC ... 435/142; 530/350; 536/23.74; 435/254.11; 435/254.21; 435/254.22; 435/254.3; 435/254.5; 435/252.3; 435/252.33; 435/254.6; 435/254.23

(58) Field of Classification Search
None
See application file for complete search history.

(56) References Cited

U.S. PATENT DOCUMENTS 6,171,831 B1   1/2001  Tsai et al.

FOREIGN PATENT DOCUMENTS

| WO | WO-00/37629   | 6/2000 |
| WO | WO-01/29073   | 4/2001 |
| WO | WO-2009/014437 | 1/2009 |

OTHER PUBLICATIONS

Database NCBI [Online], Accession No. XM_001209274, Feb. 28, 2008.
Database UniProt [Online], Accession No. Q0C8L2, Oct. 17, 2006.
Dwiarti et al., Journal of Bioscience and Bioengineering (2002) 94:29-33.
International Search Report for PCT/NL2009/050099, mailed on Jul. 7, 2009, 4 pages.
Jaklitsch et al., Journal of General Microbiology (1991) 137(3):533-539.
Magnuson et al., Advances in Fungal Biotechnology for Industry, Agriculture, and Medicine (2004) 1:307-340.
Pel et al., Nature Biotechnology (2007) 25(2):221-231.
Sauer et al., Trends in Biotechnology (2008) 26(2):100-108.
Tamano et al., Fungal Genetics and Biology (2008) 45(2):139-151.

*Primary Examiner* — Rebecca Prouty
(74) *Attorney, Agent, or Firm* — Morrison & Foerster LLP

(57) ABSTRACT

The invention relates to a nucleic acid sequence encoding an itaconate transporting Major Facilitator Superfamily Transporter (MFST) gene sequence and the protein encoded thereby. Preferably said sequence is the nucleic acid that comprises the sequence of ATEG_09972.1 of *Aspergillus terreus* or homologues thereof. Overexpression of the protein enhances the production of itaconic acid in microorganisms.

10 Claims, 6 Drawing Sheets

Figure 1:
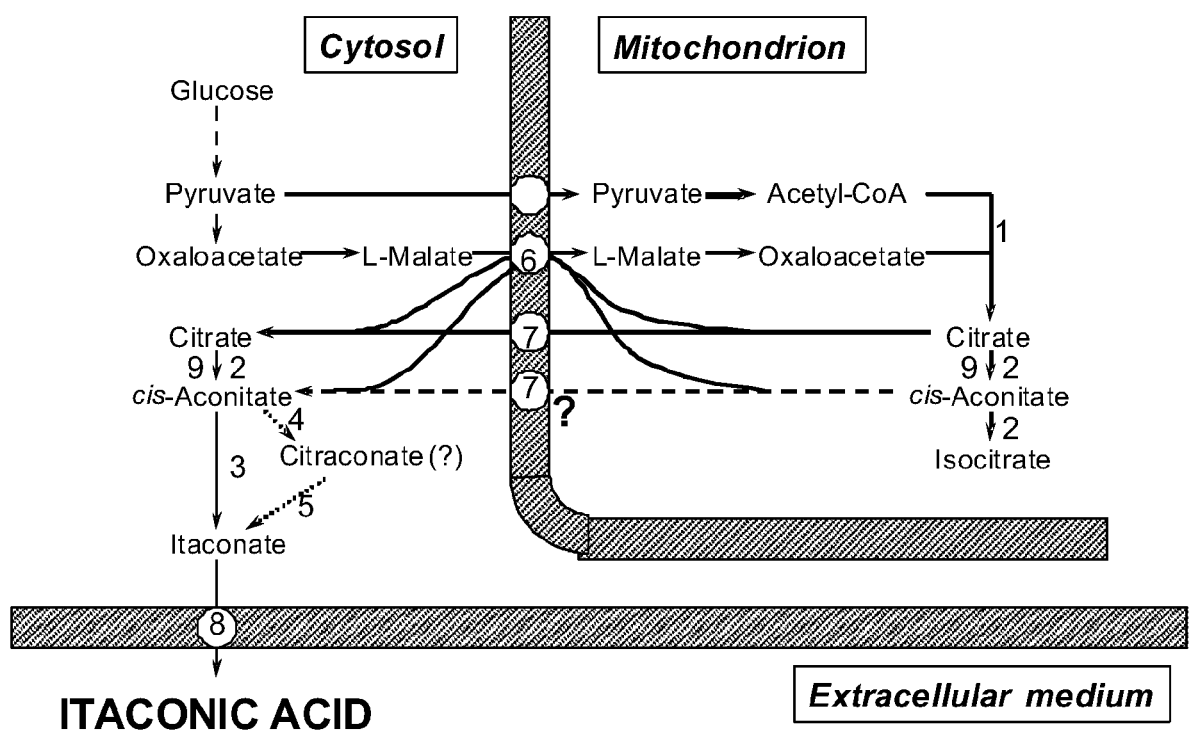

Fig. 3a Amino acid sequence of ATEG_09972.1

MGHGDTESPNPTTTTEGSGQNEPEKKGRDIPLWRKCVITFVVSWMTLVVTFSSTCLLPAA
PEIANEFDMTVETINISNAGVLVAMGYSSLIWGPMNKLVGRRTSYNLAISMLCACSAGTA
AAINEEMFIAFRVLSGLTGTSFMVSGQTVLADIFEPVYRGTAVGFFMAGTLSGPAIGPCV
GGVIVTFTSWRVIFWLQLGMSGLGLVLSLLFFPKIEGNSEKVSTAFKPTTLVTIISKFSP
TDVLKQWVYPNVFLADLCCGLLAITQYSILTSARAIFNSRFHLTTALVSGLFYLAPGAGF
LIGSLVGGKLSDRTVRRYIVKRGFRLPQDRLHSGLITLFAVLPAGTLIYGWTLQEDKGDM
VVPIIAAFFAGWGLMGSFNCLNTYVAGLFHTLIYLFPLCTCPQ*

Fig. 3b cDNA sequence of ATEG_09972.1

ATGGGCCACGGTGACACTGAGTCCCCGAACCCAACGACGACCACGGAAGGTAGCGGACAA
AACGAGCCAGAGAAAAAGGGCCGTGATATTCCATTATGGAGAAATGTGTCATTACGTTT
GTTGTTAGTTGGATGACTCTAGTCGTTACTTTCTCCAGTACTTGTCTTCTTCCTGCCGCC
CCTGAAATCGCGAATGAATTTGATATGACTGTCGAGACTATCAACATCTCCAATGCTGGT
GTCCTAGTTGCCATGGGATATTCATCCCTCATATGGGGTCCCATGAACAAGTTAGTCGGC
CGGCGGACATCATACAATCTGGCCATTTCAATGCTTTGTCATGCTCCGCTGGAACGGCA
GCGGCGATAAACGAGGAAATGTTCATAGCGTTCAGAGTGTTGAGCGGCTTAACCGGAACC
TCGTTCATGGTCTCAGGCCAAACTGTTCTTGCAGATATCTTTGAGCCTGTTTACCGTGGG
ACGGCCGTAGGTTTCTTCATGGCCGGGACTCTTTCTGGCCCTGCAATAGGCCCCTGCGTG
GGAGGGGTCATCGTCACTTTCACGAGTTGGCGTGTTATCTTCTGGCTTCAACTAGGTATG
AGCGGGCTGGGGCTCGTGCTTTCTCTGCTATTTTTCCCGAAAATCGAAGGAAATTCTGAG
AAGGTCTCAACGGCGTTTAAACCGACCACACTTGTCACAATCATATCGAAATTCTCCCCA
ACGGATGTGCTCAAGCAGTGGGTGTATCCAAATGTCTTTCTTGCCGACTTATGCTGTGGC
CTCCTGGCAATCACGCAATATTCGATCCTGACTTCAGCTCGTGCCATATTCAACTCACGA
TTTCATTTAACGACTGCCCTAGTATCGGGTCTCTTCTACCTCGCTCCAGGTGCCGGGTTC
CTGATAGGCAGTCTCGTCGGCGGTAAACTTTCGGATCGCACCGTTCGGAGATACATAGTA
AAGCGCGGATTCCGTCTCCCTCAGGATCGACTCCACAGCGGGCTCATCACATTGTTCGCC
GTGCTGCCCGCAGGAACGCTCATTTACGGGTGGACACTCCAAGAGGATAAGGGTGATATG
GTAGTGCCCATAATCGCGGCGTTCTTCGCGGGCTGGGGCTCATGGGCAGTTTTAACTGC
CTGAACACTTACGTGGCTGGTTTGTTCCACACCCTCATTTATCTATTCCCTTTGTGTACA
TGCCCACAATAA

Fig. 3c Genomic DNA sequence of ATEG_09972.1

ATGGGCCACGGTGACACTGAGTCCCCGAACCCAACGACGACCACGGAAGGTAGCGGACAA
AACGAGCCAGAGAAAAAGGGCCGTGATATTCCATTATGGAGAAAATGTGTCATTACGTTT
GTTGTTAGTTGGATGACTCTAGTCGTTACTTTCTCCAGTACTTGTCTTCTTCCTGCCGCC
CCTGAAATCGCGAATGAATTTGATATGACTGTCGAGACTATCAACATCTCCAATGCTGGT
GTCCTAGTTGCCATGGGATATTCATCCCTCATATGGGGTCCCATGAACAAGTTAGTCGGC
CGGCGGACATCATACAATCTGGCCATTTCAATGCTTTGTGCATGCTCCGCTGGAACGGCA
GCGGCGATAAACGAGGAAATGTTCATAGCGTTCAGAGTGTTGAGCGGCTTAACCGGAACC
TCGTTCATGGTCTCAGGCCAAACTGTTCTTGCAGATATCTTTGAGCCTGTACGAATCACA
CGCCCTCGTCTCCCCAATTGCGAAAACTAATCCGTTCGTGCGCAGGTTTACCGTGGGACG
GCCGTAGGTTTCTTCATGGCCGGGACTCTTTCTGGCCCTGCAATAGGTACGTACCCTGCT
GCAAGTACTAGAACTCCCAACAGGAACTAATTGTATGAGCAGGCCCCTGCGTGGGAGGGG
TCATCGTCACTTTCACGAGTTGGCGTGTTATCTTCTGGCTTCAACTAGGTATGAGCGGGC
TGGGGCTCGTGCTTTCTCTGCTATTTTTCCCGAAAATCGAAGGAAATTCTGAGAAGGTCT
CAACGGCGTTTAAACCGACCACACTTGTCACAATCATATCGAAATTCTCCCCAACGGATG
TGCTCAAGCAGTGGGTGTATCCAAATGTCTTTCTTGCCGTAAGTGTCTGGGACATATACC
CTCTGCATCTACTGGAAAACGAGATGCTCATGCCACAAATCAAAGGACTTATGCTGTGGC
CTCCTGGCAATCACGCAATATTCGATCCTGACTTCAGCTCGTGCCATATTCAACTCACGA
TTTCATTTAACGACTGCCCTAGTATCGGGTCTCTTCTACCTCGCTCCAGGTGCCGGGTTC
CTGATAGGCAGTCTCGTCGGCGGTAAACTTTCGGATCGCACCGTTCGGAGATACATAGTA
AAGCGCGGATTCCGTCTCCCTCAGGATCGACTCCACAGCGGGCTCATCACATTGTTCGCC
GTGCTGCCCGCAGGAACGCTCATTTACGGGTGGACACTCCAAGAGGATAAGGGTGATATG
GTAGTGCCCATAATCGCGGCGTTCTTCGCGGGCTGGGGGCTCATGGGCAGTTTTAACTGC
CTGAACACTTACGTGGCTGGTTTGTTCCACACCCTCATTTATCTATTCCCTTTGTGTACA
TGCCCACAATAA

Fig. 4a Amino acid sequence of A. oryzae homologue

```
MGQPDLESQTPKTIDGATKEKEEKGSKVEKGYGLPLWRKCIILFVVSWMTLAVTFSSTSL
LPATPEIAEEFNTTTETLNITNAGVLLAMGFSSLIWGPLNNLIGRRLSYNIAIFMLCVCS
AATGAAVDLKMFTAFRVLSGLTGTSFMVSGQTILADIFEPVVRGTAVGFFMAGSVSGPAI
GPCIGGLIVTFSSWRNIYWLQVGMTGFGLVLAILFVPEIKQESKEEPEEKEKRTVLSALR
LFNPLRIFRQWVYPNVFFSDLTCGLLATFQYSLLTSARSIFNPRFHLTTALISGLFYLAP
GAGFLIGSIIGGKLSDRTVRKYIVRRGFRLPQDRLNSGLVTLFAVLPVSALIYGWTLQEE
KGGMVVPILAAFFAGWGLMGSFNTLNTYVAEALPHKRSEVIAGKYIIQYIFSAGSSALVV
PIINAIGVGWTFTICVIFSIIGGLLTMATARWGLDMQQWVERKFRIHDKPGF*
```

Fig. 4b cDNA sequence of A. oryzae homologue

```
atgggtcaacccgatcttgaatctcaaaccccaaaactatagacggggccacgaaagag
aaggaagagaaaggcagcaaagttgaaaagggttacggtcttcctttgtggcggaaatgt
atcatcctcttcgtcgtcagttggatgactcttgccgttaccttctcgagcacatctctt
cttcctgcaaccccgagatcgccgaggagttcaacaccaccactgagaccctcaacatc
accaatgccggcgttttgctggctatggcttctcgtcgcttatctggggtcccttgaat
aatctgattggaagaaggctctcgtataacattgcgatcttcatgctctgtgtgttcg
gcagcgacggggctgcagtagacttgaagatgtttacggcttttcgagtgttgagcggt
ttgacggggacgtcattcatggtatcgggacagaccattctggcggacattttgaaccg
gttgtccgtggtacagccgtgggattctttatggctggatctgtctccggtcctgcaatt
gggccctgtatcggaggcctcatcgtcaccttctccagctggcgcaatatctactggctc
caagtcggcatgacaggattcggcctggttctagccattctcttcgtccccgaaatcaaa
caggaatccaaagaggaacccgaagaaaagagaagaggacagtactttcgccctacgc
ctcttcaatcccctccgaatcttcagacaatgggtctatcccaacgtcttcttctccgac
ctaacctgcggtctcctcgccacattccaatactcgctcctcacatccgcccgctcaatc
ttcaatccccgcttccacctcacaacagcactcatctccggcctcttctacctcgcccca
ggagctggcttcctgatcggcagcatcatcggcggcaaactctccgaccgtaccgtccgc
aagtacatcgtccgtcgcggcttccgattgccccaggatcgcctcaactccggcctcgtc
accctgttcgccgtgctaccgtttcggcgctgatctacggctggaccctgcaggaggag
aagggtggtatggtcgtgccgattttggcggcgttttttgcaggttgggggcttatgggc
agttttaatactttgaacacttatgttgctgaggctctgccgcataagcgctccgaagtc
atcgctggaaagtatatcatccagtatatcttttcggcggggagtagtgcgcttgtggtg
ccgattattaatgccattggggttgggtggacttttaccatttgtgtgatcttttccatc
atcggtggtctgttaacgatggctaccgcgcgatgggtctggatatgcaacaatgggtg
gagaggaagttccgcattcatgataaaccagggttttga
```

Fig. 4c Genomic DNA sequence of A. oryzae homologue

```
atgggtcaacccgatcttgaatctcaaaccccaaaactatagacggggccacgaaagag
aaggaagagaaaggcagcaaagttgaaaagggttacggtcttcctttgtggcggaaatgt
atcatcctcttcgtcgtcagttggatgactcttgccgttaccttctcgagcacatctctt
cttcctgcaaccccgagatcgccgaggagttcaacaccaccactgagaccctcaacatc
accaatgccggcgttttgctggctatgggcttctcgtcgcttatctggggtcccttgaat
aatctgattggaagaaggctctcgtataacattgcgatcttcatgctctgtgtgtgttcg
gcagcgacgggggctgcagtagacttgaagatgtttacggcttttcgagtgttgagcggt
ttgacggggacgtcattcatggtatcgggacagaccattctggcggacattttgaaccg
gtacttttcgctacctttctctatgctcctgtgtactagtcagttaagtactaataatg
gccgataggttgtccgtggtacagccgtgggattctttatggctggatctgtctccggtc
ctgcaattgggccctgtatcggaggcctcatcgtcaccttctccagctggcgcaatatct
actggctccaagtcggcatgacaggattcggcctggttctagccattctcttcgtccccg
aaatcaaacaggaatccaaagaggaacccgaagaaaaagagaagaggacagtactttccg
ccctacgcctcttcaatcccctccgaatcttcagacaatggtctatcccaacgtcttct
tctccgtaagccctccttccactaactaaaactaaaccagacctcatcaactaacaatac
ctccccaaaaaggacctaacctgcggtctcctcgccacattccaatactcgctcctcaca
tccgcccgctcaatcttcaatccccgcttccacctcacaacagcactcatctccggcctc
ttctacctcgccccaggagctggcttcctgatcggcagcatcatcggcggcaaactctcc
gaccgtaccgtccgcaagtacatcgtccgtcgcggcttccgattgcccaggatcgcctc
aactccggcctcgtcaccctgttcgccgtgctacccgtttcggcgctgatctacggctgg
accctgcaggaggagaagggtggtatggtcgtgccgattttggcggcgttttttgcaggt
tgggggcttatgggcagttttaatactttgaacacttatgttgctggtgagttttccat
ccatccatccatccatctatctttctttctttctttcttttgtttcctgtcacgtgtgca
aaggcgtggaatggttgctaataatgatacagaggctctgccgcataagcgctccgaagt
catcgctggaaagtatatcatccagtatatcttttcggcggggagtagtgcgcttgtggt
gccgattattaatgccattggggttgggtggacttttaccatttgtatgtttgaccttct
tcttcttcttcttcttcttcttcttcttcttcttcttcttcttcttcttcttcttcttct
tcttcttcttcttcttcttttttgtttgttacgggaggttatatgtgactgactaat
tgtgtaggtgtgatcttttccatcatcggtggtctgttaacgatggctaccgcgcgatgg
ggtctggatatgcaacaatgggtggagaggaagttccgcattcatgataaaccagggttt
tga
```

PRODUCTION OF ITACONIC ACID

CROSS-REFERENCE TO RELATED APPLICATIONS

This application is the national phase of PCT application PCT/NL2009/050099 having an international filing date of 4 Mar. 2009, which claims benefit of European patent application No. 08152332.6 filed 5 Mar. 2008. The contents of the above patent applications are incorporated by reference herein in their entirety.
Reference to Sequence Listing Submitted Via EFS-WEB
The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 313632010000Seqlist.txt | Nov. 29, 2010 | 50,602 bytes |

The invention relates to the field of microbial production, more specifically production of itaconic acid (itaconate), more specifically production of itaconate in micro-organisms.

Production and metabolism of itaconic acid in microbial cells has been studied extensively for several decades (Calam, C. T. et al., 1939, Thom. J. Biochem., 33:1488-1495; Bentley, R. and Thiessen, C. P., 1956, J. Biol. Chem. 226:673-720; Cooper, R. A. and Kornberg, H. L., 1964, Biochem. J., 91:82-91; Bonnarme, P. et al., 1995, J. Bacteriol. 117:3573-3578; Dwiarti, L. et al., 2002, J. Biosci. Bioeng. 1:29-33), but the metabolic pathway for itaconic acid has not been unequivocally established (Wilke, Th. and Vorlop, K.-D., 2001, Appl. Microbiol. Biotechnol. 56:289-295; Bonnarme, P. et al., 1995, J. Bacteriol. 177:3573-3578). Two complicating factors in this respect are that the biosynthesis route for itaconic acid is thought to occur both in the cytosol and the mitochondria (Jaklitsch, W. M. et al., 1991, J. Gen. Microbiol. Appl. 6:51-61) and that aconitase, the enzyme that interconverts citric acid into cis-aconitate, and vice versa, and other enzymes in the metabolic pathway have been found to be present in many isoforms in microbial cells.

Production of itaconic acid is now commercially achieved in *Aspergillus terreus*, which has physiological similarity to *A. niger* and *A. oryzae*. However, these latter two accumulate citric acid, due to the absence of cis-aconic acid decarboxylase (CAD) activity. Substrates used by these fungi include mono- and disaccharides, such as glucose, sucrose and fructose and starches, as they exist in forms that are degradable by the micro-organism, and molasses. Recently, it has been discovered that also glycerol is a useful substrate in itaconic acid production by *A. terreus* (U.S. Pat. No. 5,637,485).

The general scheme currently envisioned for itaconic acid biosynthesis is given in FIG. 1, wherein clearly the existence of the biosynthetic route both in the cytosol and the mitochondria is depicted and the connection between these two compartments. At several points of this scheme possibilities exist to try to improve the existing commercial production of itaconic acid in micro-organisms.

SUMMARY OF THE INVENTION

The invention comprises a nucleic acid sequence encoding an itaconate transporting Major Facilitator Superfamily Transporter (MFST) gene sequence (hereinafter "the itaconate transporter"). Preferably said nucleic acid comprises the ATEG_09972.1 sequence of *Aspergillus terreus* as depicted in FIG. 3B, or a nucleic acid that shares more than about 70%, preferably more than about 80%, preferably more than about 90% sequence identity with the sequence of ATEG_09972.1 as depicted in FIG. 3b. In another embodiment, the invention comprises a protein encoded by said nucleic acid.

The invention further comprises a method for the production of itaconic acid. More specifically the invention relates to improved production of itaconic acid, comprising increasing the activity of a protein capable of transporting itaconate from the cytosol to the extracellular medium, in a suitable host cell. Preferably this is achieved by overexpression of a nucleic acid sequence encoding the protein of the invention. Preferably the said nucleic acid is derived from *Aspergillus* sp. such as, *Aspergillus terreus*, *Aspergillus niger*, *Aspergillus nidulans*, *Aspergillus oryzae* or *Aspergillus fuminagates*. According to a further preferred embodiment, the said nucleic acid is expressed in a suitable vector, under control of its own or other promoters.

Also comprised in the invention is a method as described above, wherein the above described transport of itaconic acid is further increased by increasing the intracellular itaconic acid, using at least one but preferably a combination of the following methods: 1. overexpression of the gene coding for the enzyme CAD (see EP 07112895) which catabolises cis-aconitate to itaconic acid, preferably wherein said gene is encoded by the nucleic acid sequence of ATEG 09971.1; 2. overexpression of a gene coding for a protein capable of transporting di/tricarboxylate, preferably cis-aconitate, citrate or isocitrate, from the mitochondrion to the cytosol, more preferably the diacrboxylate transporter encoded by the nucleic acid sequence of ATEG 09970.1 (see EP 08151584); 3. a method as described above, wherein the activity of a regulator protein that comprises a zinc finger and a fungal specific transcription factor domain is modulated. Preferably said regulator protein is the protein encoded by the nucleic acid sequence of ATEG 09969.1, located in the same gene cluster as the transporter of the invention. By using the above method 1 also organisms that do not or hardly produce itaconic acid like *A. niger* and *A. oryzae* due to the absence of endogenous cis-aconic acid decarboxylase (CAD) activity can be used since expression of the CAD gene will cause itaconic acid production.

Another embodiment of the present invention is formed by a host cell wherein a gene coding for an itaconate transporter is introduced. Preferably said gene comprises the nucleotide sequence of the invention encoding a transporter protein. A suitable host cell preferably is a host cell selected from filamentous fungi, yeasts and bacteria, more preferably from *Escherichia coli*, *Aspergillus* sp such as *Aspergillus niger* or *Aspergillus terreus*, citrate-producing hosts or lovastatin producing hosts. The invention further comprises a host cell as described above wherein the gene coding for a protein capable of transporting di/tricarboxylate, preferably cis-aconitate, citrate or isocitrate, from the mitochondrion to the cytosol, is co-expressed. The invention further comprises a host cell as described above, wherein the transported or produced cis-aconitate is catabolised to itaconic acid by overexpression of the gene encoding the enzyme CAD.

Further, the invention pertains to the use of the protein(s) transporting itaconate from the cytosol to the extracellular medium, for the production of itaconic acid by a suitable host cell. Also comprised in the invention is the use of said protein(s) combined with the proteins transporting di/tricarboxylate over the mitochondrial membrane, the regulator protein ATEG 09969.2 and/or the use of the CAD enzyme, for the production of itaconic acid in a suitable host cell.

LEGENDS TO THE FIGURES

FIG. 1: Postulated biosynthesis route(s) for itaconic acid in *A. terreus*. 1, Citrate synthase; 2, Aconitase; 3, cis-aconitic acid decarboxylase (itaconate-forming); 4, cis-aconitic acid decarboxylase (citraconate-forming); 5, citraconate isomerase; 6, mitochondrial dicarboxylate-tricarboxylate antiporter; 7, mitochondrial tricarboxylate transporter; 8, dicarboxylate transporter; 9, 2-methylcitrate dehydratase.

Figure 2:
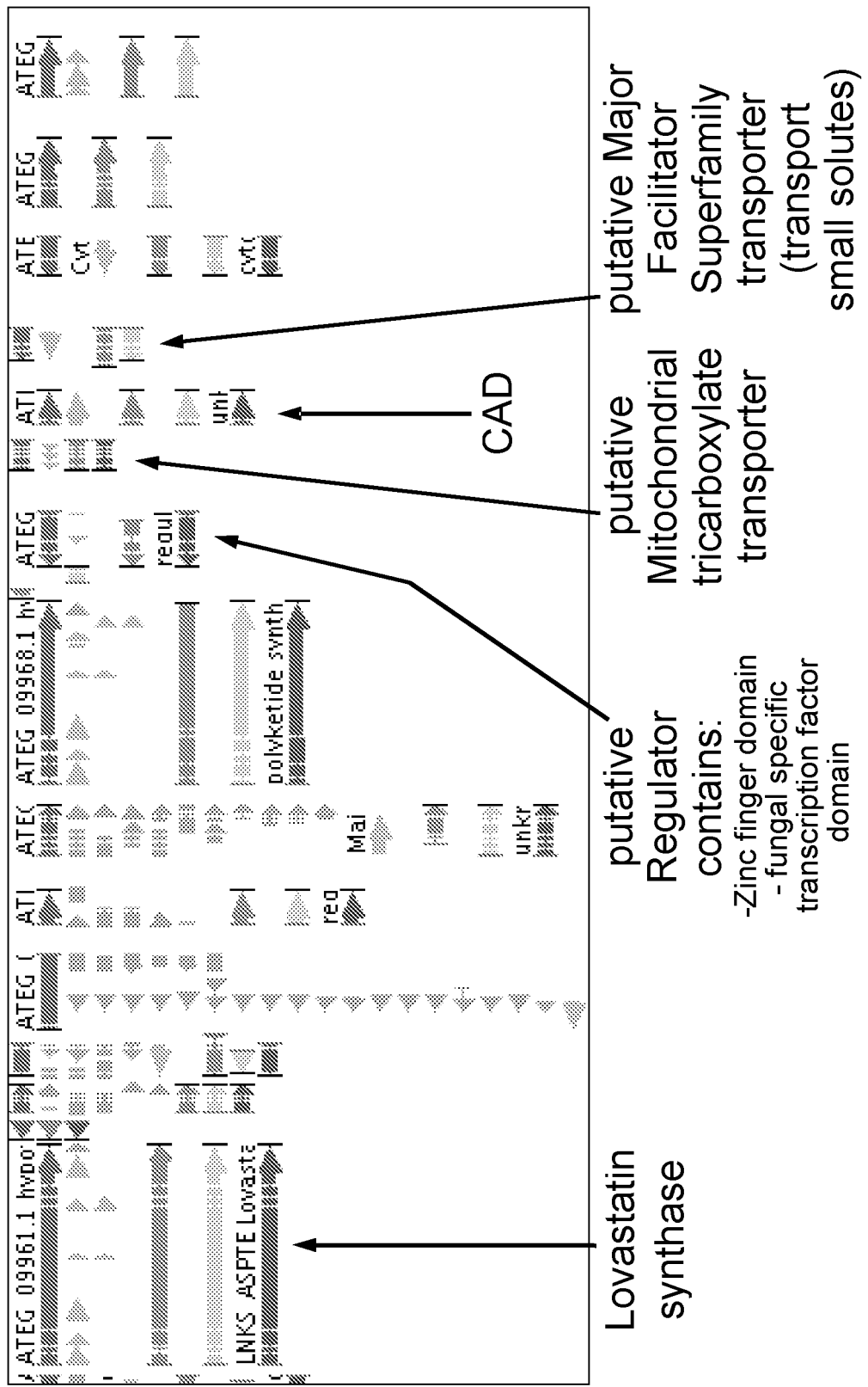

FIG. 2: Overview of *Aspergillus terreus* genome segment with the cluster of genes involved in production of itaconic acid and lovastatin ranging from ATEG 09961.1-ATEG 09975.1. The cluster contains the cis-aconitate decarboxylase (ATEG 09971.1) and the mitochondrial tricarboxylate transporter (ATEG 9970.1).

FIG. 3: Sequence of the *Aspergillus terreus* itaconate transporter: a. protein sequence (SEQ ID NO:3), b. Cdna (SEQ ID NO:2), c. genomic sequence (SEQ ID NO:1).

FIG. 4: Sequence of the *Aspergillus oryzae* itaconate transporter: a. protein sequence (SEQ ID NO:6), b. cDNA (SEQ ID NO:5), c. genomic sequence (SEQ ID NO:4).

DETAILED DESCRIPTION OF THE INVENTION

"Fungi" are herein defined as eukaryotic micro-organisms and include all species of the subdivision Eumycotina (Alexopoulos, C. J., 1962, In: Introductory Mycology, John Wiley & Sons, Inc., New York). The term fungus thus includes both filamentous fungi and yeast. "Filamentous fungi" are herein defined as eukaryotic micro-organisms that include all filamentous forms of the subdivision Eumycotina. These fungi are characterized by a vegetative mycelium composed of chitin, cellulose, and other complex polysaccharides. The filamentous fungi used in the present invention are morphologically, physiologically, and genetically distinct from yeasts. Vegetative growth by filamentous fungi is by hyphal elongation and carbon catabolism of most filamentous fungi are obligately aerobic. "Yeasts" are herein defined as eukaryotic micro-organisms and include all species of the subdivision Eumycotina that predominantly grow in unicellular form. Yeasts may either grow by budding of a unicellular thallus or may grow by fission of the organism.

The term "fungal", when referring to a protein or nucleic acid molecule thus means a protein or nucleic acid whose amino acid or nucleotide sequence, respectively, naturally occurs in a fungus.

The term "gene", as used herein, refers to a nucleic acid sequence containing a template for a nucleic acid polymerase, in eukaryotes, RNA polymerase II. Genes are transcribed into mRNAs that are then translated into protein.

"Expression" refers to the transcription of a gene into structural RNA (rRNA, tRNA) or messenger RNA (mRNA) with subsequent translation into a protein.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e., operably linked to) additional nucleic acid segments that provide for its transcription. Such additional segments may include promoter and terminator sequences, and may optionally include one or more origins of replication, one or more selectable markers, an enhancer, a polyadenylation signal, and the like.

Expression vectors are generally derived from plasmid or viral DNA, or may contain elements of both. In particular an expression vector comprises a nucleotide sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e., operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the host cell, but which has a replicon that is nonfunctional in that organism. Integration of the segment comprising the gene of interest may be selected if an appropriate marker is included within that segment.

"Transformation" and "transforming", as used herein, refer to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

By "host cell" is meant a cell that contains a vector or recombinant nucleic acid molecule and supports the replication and/or expression of the vector or recombinant nucleic acid molecule. Host cells may be prokaryotic cells such as *E. coli*, or eukaryotic cells such as yeast, fungus, plant, insect, amphibian, or mammalian cells. Preferably, host cells are fungal cells.

Key in the biosynthetic pathway for itaconic acid is the localisation of the various substrates. It is thought that production of itaconic acid mainly occurs in the cytosol (see FIG. 1). In many biochemical pathways, the end-product is inhibiting its own production to prevent excess end-product in the biological system. Excess end-product will not only lead to loss of energy in an economical sense, it can also give rise to unwanted side effects such as toxicity. It is contemplated that by depleting the cell of itaconic acid the formation of new itaconic acid will continue without end-product inhibition, thus giving—in total—an increase yield of itaconic acid. Additionally the present invention enables a more simple way of harvesting the itaconic acid due to its presence in the extracellular medium. This also enables continuous fermentation culture.

Also provided are functional homologues of the ATEG_09972.1 sequences, that are 50% or more identical to the sequence of FIG. 3b, preferably 60% or more, more preferably 70% or more, more preferably 80% or more, more preferably 90% or more and most preferably 95% or more identical. Functional in the term functional homologues means that the homologous protein has an itaconic acid/itaconate transporter function i.e. is able to transport itaconate over the cell membrane.

The term "sequence identity," as used herein, is generally expressed as a percentage and refers to the percent of amino acid residues or nucleotides, as appropriate, that are identical as between two sequences when optimally aligned. For the purposes of this invention, sequence identity means the sequence identity determined using the well-known Basic Local Alignment Search Tool (BLAST), which is publicly available through the National Cancer Institute/National Institutes of Health (Bethesda, Md.) and has been described in printed publications (see, e.g., Altschul et al., J. MoI. Biol, 215(3), 403-10 (1990)). Preferred parameters for amino acid sequences comparison using BLASTP are gap open 11.0, gap extend 1, Blosum 62 matrix.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code.

The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

The present inventors have found a method for increasing the production of itaconic acid, by increasing the activity of the protein capable of transporting itaconate from the cytosol to the extracellular medium, leading to increased recovery of itaconic acid, produced by a suitable micro-organism. The protein is further defined as a protein capable of transporting itaconic acid.

Preferably, the itaconate transporter is the itaconate transporter of *Aspergillus terreus*, as is found in the itaconate/lovastatin gene cluster (see FIG. 2), which is represented by the nucleic acid sequence found in ATEG_09972.1, which is disclosed in FIGS. 3b and 3c, for the cDNA and genomic sequence, respectively.

Further example of an itaconate transporter that could also be used in the present invention is the homologous gene denominated BAE57135.1 from *A. oryzae*, as depicted in FIGS. 4a, 4b and 4c. The produced itaconic acid can be recovered from the extracelluar medium using methods know to a person skilled in the art and as described by Wilke et al. (Wilke, Th. and Vorlop, K.-D., 2001, Appl. Microbiol. Biotechnol. 56:289-295). One preferred way of increasing the activity of said protein(s) is by overexpression of a gene(s) encoding said protein(s), preferably wherein said gene is ATEG_09972.1.

Overexpression can be effected in several ways. It can be caused by transforming the micro-organism with a gene coding for the enzyme. Alternatively, other methods can be used for effecting an increase in the activity of said enzyme. One possible way is to provide a stronger promoter in front of and regulating expression of the endogenous gene. This can be achieved by use of a strong heterologous promoter or by providing mutations in the endogenous promoter. An increased activity of the enzyme can also be caused by removing possible inhibiting regulatory proteins, e.g. by inhibiting the expression of such proteins. The person skilled in the art will know other ways of increasing the activity of the above mentioned enzyme.

The production of itaconic acid can be further optimised by combining the product secretion and recovery as described above, with overexpression of di/tricarboxylate transporters, capable of transporting, among others, cis-aconitate, citrate or isocitrate from the mitochondrion to the cytosol, preferably the gene encoded by the nucleic acid sequence of ATEG_09970.1. These subsequent processes will lead to an increase in cis-aconitate in the cytosol, which can be further converted to itaconic acid, using overexpression of the gene encoding the enzyme CAD (EC 4.1.1.6). "CAD" is defined as the enzyme, or a nucleotide sequence encoding for the enzyme cis-aconitate decarboxylase (CAD), such as the enzyme encoded by the nucleic acid sequence of ATEG_09971.1, this further comprises enzymes with similar activities (see EP07112895).

Even further optimisation of the present invention can be achieved by modulating the activity of the regulator protein that comprises a zinc finger and a fungal specific transcription factor domain as can be found on the gene cluster that also comprises ATEG_09970, wherein this regulator protein is indicated as ATEG_09969.1 (see FIG. 2).

The above described processes alone or in combination lead to a subsequent increase of itaconic acid (see FIG. 1). Another advantage of the invention is an improved method to recover the produced itaconic acid by increasing the release in the extracellular media. The combination of improved production and improved recovery leads to an increase in itaconic acid yield by a suitable host. The above described genes are preferably derived from *Aspergillus* sp. like, *Aspergillus terreus, Aspergillus niger, Aspergillus nidulans, Aspergillus oryzae* or *Aspergillus fuminagates*. However, it is also possible to derive the gene from other itaconate producing micro-organisms such as *Ustilago zeae, Ustilago maydis, Ustilago* sp., *Pseudozyma antarctica, Candida* sp., *Yarrowia lipolytica,* and *Rhodotorula* sp.

In another aspect of the invention, micro-organisms overexpressing at least one but alternatively a combination of the above mentioned nucleotide sequences, encoding at least a protein capable of transporting itaconate from the cytosol to the extracellular medium, are produced and used for increased production of itaconic acid. More preferably micro-organisms overexpressing a protein that transports itaconate combined with protein(s) that transport di/tricarboxylates from the mitochondrion to the cytosol and/or the CAD enzyme are used to further improve the production of itaconic acid.

Micro-organisms used in the invention are preferably micro-organisms that naturally produce itaconic acid. Preferably overexpression of the genes encoding the above described protein(s) and enzyme(s) is accomplished in filamentous fungi, yeasts and/or bacteria, such as, but not limited to *Aspergillus* sp., such as the fungi *A. terreus, A. itaconicus* and *A. niger, Aspergillus nidulans, Aspergillus oryzae* or *Aspergillus fuminagates, Ustilago zeae, Ustilago maydis, Ustilago* sp., *Candida* sp., *Yarrowia lipolytica, Rhodotorula* sp. and *Pseudozyma antarctica,* the bacterium *E. coli* and the yeast *Saccharomyces cerevisiae*. Especially preferred are heterologous citric acid producing organisms in which the substrates are available in the host organism.

Recently (see US 2004/0033570) it has also been established that the so-called D4B segment of *Aspergillus terreus*, which comprises the CAD gene is responsible for the synthesis of lovastatin (see FIG. 2). Thus, it is submitted that also these micro-organisms which are known to produce lovastatin would be suitable candidates for the production of itaconic acid. Such micro-organisms include *Monascus* spp. (such as *M. ruber, M. purpureus, M. pilosus, M. vitreus* and *M. pubig-*

*erus*), *Penicillium* spp. (such as *P. citrinum, P. chrysogenum*), *Hypomyces* spp., *Doratomyces* spp. (such as *D. stemonitis*), *Phoma* spp., *Eupenicillium* spp., *Gymnoascus* spp., *Pichia labacensis, Candida cariosilognicola, Paecilomyces virioti, Scopulariopsis brevicaulis* and *Trichoderma* spp. (such as *T. viride*).

Consequently also the CAD encoding part of the D4B segment and the enzyme with CAD activity for which it codes from these above-mentioned lovastatin producing micro-organisms are deemed to be suitable for use in the present invention. It further is contemplated that a heterologous organism, which in nature does not or hardly produce itaconic acid like *Aspergillus niger* or *Aspergillus oryzae* can be used when providing such an organism with a functional pathway for expression of itaconic acid, by overexpression of the above mentioned genes.

Recombinant host cells described above can be obtained using methods known in the art for providing cells with recombinant nucleic acids. These include transformation, transconjugation, transfection or electroporation of a host cell with a suitable plasmid (also referred to as vector) comprising the nucleic acid construct of interest operationally coupled to a promoter sequence to drive expression. Host cells of the invention are preferably transformed with a nucleic acid construct as further defined below and may comprise a single but preferably comprises multiple copies of the nucleic acid construct. The nucleic acid construct may be maintained episomally and thus comprise a sequence for autonomous replication, such as an ARS sequence. Suitable episomal nucleic acid constructs may e.g. be based on the yeast 2µ or pKD1 (Fleer et al., 1991, Biotechnology 9: 968-975) plasmids. Preferably, however, the nucleic acid construct is integrated in one or more copies into the genome of the host cell. Integration into the host cell's genome may occur at random by illegitimate recombination but preferably the nucleic acid construct is integrated into the host cell's genome by homologous recombination as is well known in the art of fungal molecular genetics (see e.g. WO 90/14423, EP-A-0 481 008, EP-A-0 635 574 and U.S. Pat. No. 6,265,186) Most preferably for homologous recombination the ku70Δ/ku80Δ techniques is used as described for instance in WO 02/052026 and Krappmann, 2007, Fungal Biol. Rev. 21:25-29).

Transformation of host cells with the nucleic acid constructs of the invention and additional genetic modification of the fungal host cells of the invention as described above may be carried out by methods well known in the art. Such methods are e.g. known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

In another aspect the invention relates to a nucleic acid construct comprising a nucleotide sequence encoding at least an itaconate transporter as defined above and usable for transformation of a host cell as defined above. In the nucleic acid construct, the coding nucleotide sequence(s) preferably is/are operably linked to a promoter for control and initiation of transcription of the nucleotide sequence in a host cell as defined below. The promoter preferably is capable of causing sufficient expression of the itaconate transporters transporting itaconate from the cytosol to the extracellular medium and/or the di/tricarboxylate transporters transporting tricarboxylates from the mitochondrion and/or the CAD enzyme(s), described above, in the host cell. Promoters useful in the nucleic acid constructs of the invention include the promoter that in nature provides for expression of the coding genes. Further, both constitutive and inducible natural promoters as well as engineered promoters can be used. Promoters suitable to drive expression of the genes in the hosts of the invention include e.g. promoters from glycolytic genes (e.g. from a glyceraldehyde-3-phosphate dehydrogenase gene), ribosomal protein encoding gene promoters, alcohol dehydrogenase promoters (ADH1, ADH4, and the like), promoters from genes encoding amylo- or cellulolytic enzymes (glucoamylase, TAKA-amylase and cellobiohydrolase). Other promoters, both constitutive and inducible and enhancers or upstream activating sequences will be known to those of skill in the art. The promoters used in the nucleic acid constructs of the present invention may be modified, if desired, to affect their control characteristics. Preferably, the promoter used in the nucleic acid construct for expression of the genes is homologous to the host cell in which genes are expressed.

In the nucleic acid construct, the 3'-end of the coding nucleotide acid sequence(s) preferably is/are operably linked to a transcription terminator sequence. Preferably the terminator sequence is operable in a host cell of choice. In any case the choice of the terminator is not critical; it may e.g. be from any fungal gene, although terminators may sometimes work if from a non-fungal, eukaryotic, gene. The transcription termination sequence further preferably comprises a polyadenylation signal.

Optionally, a selectable marker may be present in the nucleic acid construct. As used herein, the term "marker" refers to a gene encoding a trait or a phenotype which permits the selection of, or the screening for, a host cell containing the marker. A variety of selectable marker genes are available for use in the transformation of fungi. Suitable markers include auxotrophic marker genes involved in amino acid or nucleotide metabolism, such as e.g. genes encoding ornithine-transcarbamylases (argB), orotidine-5'-decarboxylases (pyrG, URA3) or glutamine-amido-transferase indoleglycerol-phosphate-synthase phosphoribosyl-anthranilate isomerases (trpC), or involved in carbon or nitrogen metabolism, such e.g. niaD or facA, and antibiotic resistance markers such as genes providing resistance against phleomycin, bleomycin or neomycin (G418). Preferably, bidirectional selection markers are used for which both a positive and a negative genetic selection is possible. Examples of such bidirectional markers are the pyrG (URA3), facA and amdS genes. Due to their bidirectionality these markers can be deleted from transformed filamentous fungus while leaving the introduced recombinant DNA molecule in place, in order to obtain fungi that do not contain selectable markers. This essence of this MARKER GENE FREE™ transformation technology is disclosed in EP-A-0 635 574, which is herein incorporated by reference. Of these selectable markers the use of dominant and bidirectional selectable markers such as acetamidase genes like the amdS genes of *A. nidulans, A. niger* and *P. chrysogenum* is most preferred. In addition to their bidirectionality these markers provide the advantage that they are dominant selectable markers that, the use of which does not require mutant (auxotrophic) strains, but which can be used directly in wild type strains.

Optional further elements that may be present in the nucleic acid constructs of the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence. Suitable episomal nucleic acid constructs may e.g. be based on the yeast 2μ or pKD1 (Fleer et al., 1991, Biotechnology 9: 968-975) plasmids. Alternatively the nucleic acid construct may comprise sequences for integration, preferably by homologous recombination (see e.g. WO98/46772). Such sequences may thus be sequences homologous to the target site for integration in the host cell's genome. The nucleic acid constructs of the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987).

In a further aspect the invention relates to fermentation processes in which the transformed host cells of the invention are used for the conversion of a substrate into itaconic acid. A preferred fermentation process is an aerobic fermentation process. The fermentation process may either be a submerged or a solid state fermentation process.

In a solid state fermentation process (sometimes referred to as semi-solid state fermentation) the transformed host cells are fermenting on a solid medium that provides anchorage points for the fungus in the absence of any freely flowing substance. The amount of water in the solid medium can be any amount of water. For example, the solid medium could be almost dry, or it could be slushy. A person skilled in the art knows that the terms "solid state fermentation" and "semi-solid state fermentation" are interchangeable. A wide variety of solid state fermentation devices have previously been described (for review see, Larroche et al., "Special Transformation Processes Using Fungal Spores and Immobilized Cells", Adv. Biochem. Eng. Biotech., (1997), Vol 55, pp. 179; Roussos et al., "Zymotis: A large Scale Solid State Fermenter", Applied Biochemistry and Biotechnology, (1993), Vol. 42, pp. 37-52; Smits et al., "Solid-State Fermentation-A Mini Review, 1998), Agro-Food-Industry Hi-Tech, March/April, pp. 29-36). These devices fall within two categories, those categories being static systems and agitated systems. In static systems, the solid media is stationary throughout the fermentation process. Examples of static systems used for solid state fermentation include flasks, petri dishes, trays, fixed bed columns, and ovens. Agitated systems provide a means for mixing the solid media during the fermentation process. One example of an agitated system is a rotating drum (Larroche et al., supra). In a submerged fermentation process on the other hand, the transformed fungal host cells are fermenting while being submerged in a liquid medium, usually in a stirred tank fermenter as are well known in the art, although also other types of fermenters such as e.g. airlift-type fermenters may also be applied (see e.g. U.S. Pat. No. 6,746,862).

Preferred in the invention is a submerged fermentation process, which is performed in a fed-batch or repeated (fed-) batch mode. In a fed-batch fermentation there is a continuous input of feed containing a carbon source and/or other relevant nutrients in order to improve itaconic acid yields. The input of the feed can, for example, be at a constant rate or when the concentration of a specific substrate or fermentation parameter falls below some set point. In a repeated batch fermentation the culture is harvested at regular time-intervals by stopping the fermentation and retrieving the produced product from the medium. Next to refreshing the medium often also part of the microbial culture is discarded, while the rest is used as a new inoculum for a following batch culture.

It is preferred to use a host cell that naturally would contain the enzymes/transporters of the itaconic acid pathway as depicted in FIG. 1, and the enzymes/transporters of the citric acid pathways in the cytosol and mitochondrion. However, if the host would lack one or more of these genes, they can be co-introduced with the above described enzymes and proteins. Such a co-introduction can be performed by placing the nucleotide sequence of such a gene on the same plasmid vector as the above described genes, or on a separate plasmid vector.

Further, since the itaconic acid pathway is located partly in the cytosol and partly in the mitochondrion, it is contemplated that overexpression of the genes/enzymes in either or both of those compartments would be desirable. The person skilled in the art will know how to achieve overexpression in the cytosol or mitochondria by using the appropriate signal sequences.

EXAMPLES

Example 1

Construction of Micro-Array

An anonymous clone/EST-based array approach was taken according to the following scheme:

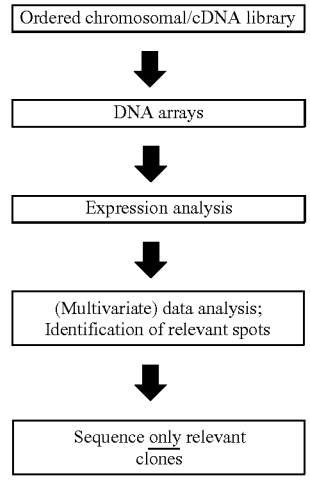

An *A. terreus* micro-array was made composed of a clone-based and an EST-based array.
Materials and Methods Construction Micro-Array
Isolation of Chromosomal DNA from *A. Terreus*

*A. terreus* was cultivated overnight in a shake flask in enriched minimal medium at 33° C. and 250 rpm. Enriched minimal medium (pH 5.5) is mineral medium (MM) supplemented with 0.5% yeast extract and 0.2% casamino acids. The composition of MM was: 0.07 M NaNO$_3$, 7 mM KCl, 0.11 M KH$_2$PO$_4$, 2 mM MgSO$_4$, and 1 ml/l of trace elements (1000*stock solution: 67 mM ZnSO$_4$, 178 mM H$_3$BO$_3$, 25 mM MnCl$_2$, 18 mM FeSO$_4$, 7.1 mM CoCl$_2$, 6.4 mM CuSO$_4$, 6.2 mM Na$_2$MoO$_4$, 174 mM EDTA).

Mycelium was harvested after 22 hours and frozen in liquid nitrogen. Chromosomal DNA was isolated from 4.5 g mycelium following the protocol described below.

Grind 0.5-1.0 g mycelium under liquid nitrogen using the membrane disrupter.
Place polypropylene tubes (Greiner) with 1.5 ml water-saturated phenol, 1 ml TNS, 1 ml PAS and 0.5 ml 5×RNB in a water bath at 55° C., add the still frozen mycelium to the tubes and vortex every 20 seconds for totally 2-4 minutes.

TNS: triisopropyl naphthalene sulphonic acid, 20 mg/ml in water, freshly prepared PAS: 4 aminosalisylic acid, 120 mg/ml in water, freshly prepared 5×RNB: 60.55 g Tris, 36.52 g NaCl, 47.55 g EGTA in 500 ml water (pH=8.5)

Add 1 ml sevag (24:1 chloroform:isoamyl alcohol) and vortex with intervals for another 1-2 minutes.

Spin for 10 min. in the tabletop centrifuge at 4° C. at maximum velocity.

Extract the water-phase once again with phenol-sevag and twice with sevag. GENTLY, AVOID SHEARING!

Precipitate the DNA with 2 volumes ethanol. Spin directly for 10 min. in the tabletop centrifuge.

Drain the tube, dry it with Kleenex and resuspend the pellet in 500 µl Tris/EDTA. Transfer to a microvial.

Extract with phenol-sevag until interface stays clean. Then extract once with sevag.

Precipitate with 2 volumes ice-cold ethanol, spin down and resuspend the pellet in 100-200 µl TE with 50 µg/ml RNase.

Construction of Clone-Based gDNA Library

The gDNA library was prepared as follows:

Chromosomal *A. terreus* DNA was sheared into fragments of size 1.5-2.5 kb

The sheared DNA was subsequently size fractionated, end-repaired (Lucigen), and ligated into blunt-end pSMART-HC-Amp vectors (Lucigen).

The ligated constructs were transformed into *E. coli* DH 10b

Colony PCR was performed on 96 transformants to check that >90% of the inserts had the correct size Sequence analysis (short run) was performed on 20 clones to confirm their diversity and fungal origin Colony picking of 20,000 amp-resistant colonies was carried out into 96-well microtiter plates containing TY medium+100 µg/ml ampicillin The 20.000 clones were replicated into 96-well microtiter plates. The ordered libraries are stored as glycerol stocks at −80° C.

Generation of mRNA for cDNA Library Construction

Precultures: *A. terreus* spores ($10^6$-$10^7$/ml) were inoculated into 100 ml B medium (2 g/l NH4NO3; 1 g/l MgSo4*7H2O; 0.008 g/l ZnSO4*7H2O; 0.015 g/l CuSO4*5H2O; 1.5 ppm FeSO4*5H2O; 0.08 g/l KH2PO4; 10 g/l CaCl2*2H2O, set to pH 3.1 with HCl) containing 20 g/l glucose, and incubated for 24-48 hours at 37° C. at 250 rpm. Production cultures (B medium containing 100 g/l glucose) were inoculated 1/10 (v/v) for 2-days cultivations and 1/25 (v/v) for 3-day cultivations. After 2-3 days cultivation mycelium was harvested, filtered over miracloth, washed with 0.2 M sodium phosphate buffer (pH 6.5), frozen in liquid nitrogen and stored at −80° C.

Isolation of mRNA from *A. Terreus* grind mycelium with mortar and pestle under liquid nitrogen; add 100 µl β-mercaptoethanol before grinding to inactivate RNAse transfer powder to cooled plastic tube (1.0 g per tube); keep mycelium frozen add 4 ml Trizol and vortex till homogenous add 0.4 ml chloroform and vortex centrifuge for 20-30 min. at 3700 rpm, 4° C.

transfer supernatant to Eppendorf tubes (1.2 ml per tube)

add 0.7 ml per 1.2 ml supernatant centrifuge in eppendorf centrifuge for 15 min. at 14.000 rpm, 4° C.

wash pellet with 1 ml 70% ethanol centrifuge 5 min., 14.000 rpm, 4° C.

air-dry pellet and resuspend in 0.2 ml water store RNA samples at −80° C.

Construction of cDNA library

The cDNA library was prepared as follows:

The RNA was run on gel to determine the quality of the sample polyT-primed cDNA was prepared from the total RNA provided (RT-PCR reaction using superscript and dT primers The cDNA was size fractionated to give fragments of size 1.0-1.5 kb The fragments were end-repaired (Lucigen), and ligated into blunt-end p SMART-HC-kan vectors (Lucigen).

Restriction analysis of 96 clones was performed to check the insert size and the % of transformants which had the correct insert size Sequence analysis (short run) of 20 clones was performed to confirm diversity and fungal origin 5,000 kanamycin-resistant colonies were picked into microtiter plates The 5000 cDNA clones were replicated into 96-well microtiter plates. The ordered libraries were stored as glycerol stocks at −80° C.

Construction of the *A. Terreus* Clone-Based Array

PCR fragments were generated from the different clones from the gDNA (20,000 clones) and cDNA (5,000 clones) library by mass 96 well PCR (50 µl/well, Lucigen SMART-SR1/SL1 primers with 5'-C6-aminolinkers, SuperTaq and buffer from HT Biotech. Ltd, dNTP's (Roche 11 969 064 001), pintool dipped template from grown colony plates).

All above PCR products were purified by 96 well precipitation (isopropanol and 96% ethanol wash), speedvac dried, dissolved in 15 µl 3×SSC/well and spotted with quill pins (Telechem SMP3) on CSS100 silylated aldehyde glass slides (Telechem, USA) using a SDDC2 Eurogridder (ESI, Canada). During spotting, aminolinkers of PCR products will covalently link with aldehyde groups of the coated slides.

gDNA and cDNA PCR products were spotted on two separate slides (slide a: 1st 10,000 gDNA's+5000 cDNA's; slide b: 2nd 10,000 gDNA's+same 5000 cDNA's).

For the clone-based array a genomic library was constructed. A total of 20,000 clones containing chromosomal fragments was generated, 90% of which had an average insert size of 1.5-2.5 kb. This resulted in a full genome coverage of 64% (Akopyants et al., 2001).

For the EST-based array a cDNA library of in total 5000 cDNA clones was constructed, 70% of which had an average insert size of 1.0-1.5 kb. This so-called EST-based approach has the advantage that it will be enriched for the genes expressed under the selected (itaconic acid producing) conditions. Moreover, in the EST-based approach per clone (and thus spot) only a single gene is represented in eukaryotes.

The complete micro-array, thus consisting of 20,000 genomic DNA clones and 5,000 cDNA clones was composed of an A and a B glass slide. Both slides contained the same 5,000 cDNA spots. The A and B slide each contained 10,000 of the gDNA spots.

Example 2

Generation of the Different RNA Samples by Fermentation

Materials and Methods Fermentation and mRNA Isolation
Fermentation Conditions of *A. Terreus*

5-Liter controlled batch fermentations were performed in a New Brunswick Scientific Bioflow 3000 fermentors. The following conditions were used unless stated otherwise:

37° C.

pH start 3.5 set point 2.3

DO set points Day 1: 75%

Day 2, 3, 4: 50%

Subsequent days: 25%

Preculture: 100 ml of the same medium as used in the fermentation medium ($10^7$ spores/ml) in 500 ml Erlenmeyer flask with baffles, overnight, 37° C., 150 rpm
pH control: 4M KOH (Base), 1.5 M $H_3PO_4$ (Acid)
Antifoam: Struktol (Schill & Seilacher)
Fermentation Medium Compositions:
Per liter: 2.36 g of $NH_4SO_4$, 0.11 g of $KH_2PO_4$, 2.08 g of $MgSO_4*7H_2O$, 0.13 g of $CaCl_2*2H_2O$, 0.074 g of NaCl, 0.2 mg of $CuSO_4*5H_2O$, 5.5 mg of Fe(III) $SO_4*7H_2O$, 0.7 mg of $MnCl_2*4H_2O$ and 1.3 mg of $ZnSO_4*7H_2O$ and 100 g of glucose as a carbon source.
All media were prepared in demineralised water.
Isolation of mRNA from *A. Terreus*
See mRNA isolation protocol described in Example 1
Determination of the Itaconate Concentration by HPLC
5 µl of a 10-times diluted supernatant sample (split ratio 1:3) was separated using a Waters 2695 Separations module on a reversed-phase Develosil 3 µm RP-Aqueous C30 140A column (150×3 mm) (Phenomenex p/n CH0-6001) at 25° C. using the solvent gradient profile (flow rate was 0.4 ml/min) shown in Table 1.

TABLE 1

Solvent gradient of the RP-UV method.

| Time (min) | A (20 mM $NaH_2PO_4$ pH 2.25) (%) | B (Acetonitril) (%) |
|---|---|---|
| 0 | 100 | 0 |
| 10 | 100 | 0 |
| 15 | 95 | 5 |
| 20 | 95 | 5 |
| 21 | 100 | 0 |
| 30 | 100 | 0 |

Compounds were detected by UV at 210 nm using a Waters 2487 Dual wavelength Absorbance detector (Milford, MA, USA).

Itaconate Productivity

Itaconate productivity at a certain time point was calculated as the slope of the regression line between that particular time point and the time points right before and after that time point. To this end of 6-10 supernatant samples of the different fermentations, the itaconate concentrations were determined by HPLC.

For the transcriptomics approach it is essential to have RNA samples from fermentations that result in the production of different amounts of itaconate. Therefore a literature survey was performed in order to identify medium components and/or physicochemical conditions that affect the amount of itaconate produced by *A. terreus*. Although many conflicting reports were found regarding the effect that a specific parameter has on itaconic acid production, 4 key overall parameters were identified from this literature survey, i.e. (i) carbon source, (ii) pH, (iii) trace element (i.e. Mn) concentration and (iv) oxygen tension. Fermentations with *A. terreus* varying principally in these four parameters were performed on a mineral salts medium to ensure that the elemental limitations required for itaconate production would be achieved. Table 2 presents an overview of the fermentations performed in this study.

TABLE 2

Overview of the fermentations performed in order to generate RNA samples for transcriptome analysis.

| Fermentation run | Fermentation | Environmental condition | Max. Itaconic acid (g/l) | Max. Biomass (gDWT/kg) |
|---|---|---|---|---|
| First Run | 1 | Glucose (100 g/l) (control) | 16.1 | 12.7 |
| | 2 | Fructose as C-source | 8.84 | 13.7 |
| | 3 | Maltose as C-source | 13.9 | 12.1 |
| Second run | 4 | Glucose (100 g/l) pH start 3.5, set point 2.3 (control) | 25.8 | 11.6 |
| | 5 | pH set 3.5 | 8.7 | 16.5 |
| | 6 | pH start 3.5 no set point | 30.6 | 8.7 |
| Third run | 7 | Low glucose (30 g/l) | 11.1 | 6.7 |
| | 8 | $O_2$ set point 25% | 47.2 | 12.0 |
| | 9 | 5* higher Mn | 20.3 | 13.8 |
| Fourth run | 10 | Glucose (100 g/l) (control) | 26.9 | 17.9 |
| | 11 | pH set 4.5 | 0.1 | 20.4 |
| | 12 | $O_2$ set point 10% | 52.9 | 10.6 |

The reference fermentation is on 100 g/l glucose, dO2, day 1, 75%; day 2-4, 50%, day 5 and further 25%, pH start 3.5, set point at 2.3.

As shown in Table 2, a considerable variation in the amount of itaconate is produced in this set of fermentations, ranging from almost no itaconate (fermentation #11; pH 4.5) to about 50 g/l itaconate (#8 and #12; 02 set point 25% and 10% respectively).

Of each fermentation 2 to 5 samples were harvested for isolation of mRNA.

From in total 23 fermentation samples mRNA could be isolated. Of 7 samples, mRNA was isolated twice independently. It proved to be especially difficult (impossible) to extract RNA from the samples taken in the stationary phase. A number of samples showed partial degradation of the RNA. Although no mRNA could be isolated from the samples from fermentations #6 and #12, the remaining samples still covered the complete range of itaconate production (Table 3).

TABLE 3

List of 30 mRNA samples from various fermentation conditions that were used for transcriptome analysis. The samples marked with asterix were the samples used for the differential expression data analysis.

| Sample no. | Fermentation condition | RNA id | EFT (hours) | Itaconic acid (g/l) | Itaconic acid Productivity | RNA quality |
|---|---|---|---|---|---|---|
| R3 | gluc100 | 1.3.a | 50.3 | 14.6 | 0.117 | ok |
| R4 | gluc100 | 1.4.a | 74.8 | 16.1 | 0.060 | ok |
| R5 | fruc100 | 2.3.a | 50.3 | 8.2 | 0.082 | ok |
| R6 | fruc100 | 2.3.b | 50.3 | 8.2 | 0.082 | ok |
| R7 | fruc100 | 2.4.a | 75.05 | 8.6 | −0.013 | ok |
| R8 | malt100 | 3.3.a | 50.3 | 7 | 0.355 | ok |

TABLE 3-continued

List of 30 mRNA samples from various fermentation conditions that were used for transcriptome analysis. The samples marked with asterix were the samples used for the differential expression data analysis.

| Sample no. | Fermentation condition | RNA id | EFT (hours) | Itaconic acid (g/l) | Itaconic acid Productivity | RNA quality |
|---|---|---|---|---|---|---|
| R9 | malt100 | 3.4.a | 75 | 12.1 | 0.220 | ok |
| R10 | pH-i3.5 | 4.3.a | 53.25 | 25.8 | 0.146 | part degr |
| R11 | pH-i3.5 | 4.3.b | 53.25 | 25.8 | 0.146 | part degr |
| R12 | pH-i3.5 | 4.4.a | 73 | 24 | −0.153* | ok |
| R13 | pH-c3.5 | 5.3.a | 53.5 | 7.5 | −0.042 | ok |
| R14 | pH-c3.5 | 5.3.b | 53.5 | 7.5 | −0.042 | ok |
| R15 | pH-c3.5 | 5.4.a | 73.25 | 7.9 | 0.035 | ok |
| R16 | gluc30 | 7.2.a | 30.25 | 9 | 0.317 | ok |
| R1 | gluc30 | 7.3.a | 43.5 | 10 | 0.030 | ok |
| R17 | gluc30 | 7.3.a | 43.5 | 10 | 0.030 | ok |
| R18 | O2s25% | 8.2.a | 30.5 | 36* | 0.824* | ok |
| R19 | O2s25% | 8.4.a | 78.25 | 46 | 0.029 | part degr |
| R20 | 5xMn | 9.2.a | 30.75 | 1 | 0.194 | ok |
| R21 | 5xMn | 9.2.b | 30.75 | 1 | 0.194 | ok |
| R22 | 5xMn | 9.3.a | 53.5 | 10 | 0.496 | part degr |
| R23 | 5xMn | 9.3.b | 53.5 | 10 | 0.496 | part degr |
| R24 | 5xMn | 9.4.a | 78.5 | 19 | 0.189 | part degr |
| R25 | 5xMn | 9.4.b | 78.5 | 19 | 0.189 | part degr |
| R26 | 5xMn | 9.5.a | 93.25 | 20 | 0.106 | ok |
| R2 | Gluc100 | 10.3.a | 51.5 | 14.7 | 0.256 | ok |
| R27 | Gluc100 | 10.3.a | 51.5 | 14.7 | 0.256 | ok |
| R28 | Gluc100 | 10.4.a | 74 | 19.5 | 0.085 | ok |
| R29 | Gluc100 | 10.5.a | 100.4 | 22 | 0.177 | part degr |
| R30 | Gluc100 | 10.5.b | 100.4 | 22 | 0.177 | part degr |
| R31 | pH 4.5 | 11.3.a | 51.5 | 0.04* | −0.001 | ok |
| R32 | pH 4.5 | 11.4.a | 74 | 0.05* | 0.003 | ok |

Example 3

Transcriptome Analysis, Data Analysis of the Array Data

Materials and Methods Transcriptome Analysis, Data Normalization and Data Analysis
Labeling of RNA and gDNA Total RNA's (5 µg/30 µl reaction), isolated from various *A. terreus* cultures (strain NRRL 1960, BASF) with differential itaconate production, were labelled with amino-allyl-dUTP (0.75 µM aa-dUTP final conc., Sigma A0410), using 3 µl 50 µM oligo p(dT)$_{15}$ primer (La Roche, 814270), unlabelled dNTP's (added to 1.25 µM final conc. for each dNTP), 2 µl Superscript II Reverse Transcriptase and buffer (Life Technologies, 10297-018: primer annealing 10 min 70° C., transcriptase 180 min 42°). After RNA hydrolysis (3 µl 2.5M NaOH, 30 min 37°, 3 µl 2.5 M HAc) the aa-dUTP labelled cDNA was directly purified (below).

As a reference for correcting slide differences (spotting, labeling-, hybridization- and scan efficiency), gDNA (0.5 µg/reaction) of *Aspergillus terreus* (strain NRRL 1960, BASF) was labelled with aa-dUTP, using dNTP's (conc. as above), Klenov-DNA Polymerase and buffer (Bioprime kit, Invitrogen 18094-011: primer annealing 5 min 96° C., polymerase 90 min 37°).

The aa-dUTP-labelled cDNA or gDNA was purified (QIAquick column, Qiagen 28106), speedvac dried, dissolved (4.5 µl 0.1 M Na$_2$CO$_3$), coupled with 4.5 µl Cy5-NHS-ester for cDNA, or 4.5 µl Cy3-NHS-ester for gDNA (Amersham/GE-Healthcare PA25001 or PA23001 respectively, each in 73 µl DMSO) for 60 min at 20° C., diluted with 10 µl of water, and again purified on Autoseq G50 columns (GE-Healthcare 27-5340).

Array Blocking, (Pre) Hybridization and Image Analysis

Before hybridization with the array produced as described above, slides were blocked (removal surplus of spotted PCR products and blocking of free aldehyde groups) by 3× quickly washing (20° C.) with Prehyb buffer and 45 min incubation (42° C.) in PreHyb buffer (5×SSC, 1% BSA, 0.1% SDS). After 4 washes in water, spotted PCR products were denatured by dipping the slides 5 sec in boiling water and drying them with a N$_2$-gas-pistol.

The Cy5- and Cy3-labelled sample were combined, 8 µl 25 µg/µl yeast tRNA (Invitrogen, 15401-029) and 4 µl 5 µg/µl poly-dA/dT (Amersham 27-7860) were added, the mixture was speed vac dried, dissolved in 160 µl Easyhyb buffer (Roche, 1 796 895), denatured (2 min, 96° C.), cooled to 50° C., applied on a pair of prehybridised slides (a+b, 80 µl/slide) prewarmed at 50° C., covered with a cover slide (Hybri slibs, Mol. Probes. H-18201) and incubated overnight at 42° C. in a humidified hybridization chamber (Corning 2551). Slides were washed (pair a+b in one 50 ml tube, 1× in 1×SSC/0.1% SDS 37° C., 1× in 0.5×SSC 37° C., 2× in 0.2×SSC 20° C.) and dried with N$_2$-gas. All pre-hybridisation buffers were 0.45 µm filtered to reduce dust noise. Slide images of Cy5- and Cy3-fluorescence intensity (ScanArray Express Scanner & Software, Packard Biosc.) were analysed (Imagene 5.6 Software, Biodiscovery) to obtain for each spot signal- and local background value (medians) for the hybridized Cy5-RNA and Cy3-reference gDNA. These values were used for further data analysis.

Array Data Normalization

Before normalization, all low abundant spots having a Signal/Background below 1.5 were removed. Data were normalized using a total cDNA signal correction. For each slide and each spot, the difference between signal and background was calculated for Cy5 and Cy3. Per slide, the sum of the differences was taken for Cy5 and Cy3, and the ratio between these two was used as normalisation factor for that particular slide. All spots (chromosomal and genomic) were normalised using this total cDNA signal.

Data Analysis of the Transcriptomics Data by Multivariate Regression Analysis

Scaling

Data were range scaled $[(x-\bar{x})/(x_{max}-x_{min})]$ (van den Berg et al., 2006, BMC Genomics 7:142) in the statistical analysis. Mathematically, range-scaling means that every element of column i is divided by the range of column i. The range of column i is the difference between the maximum and minimum value of all elements of column i. Subsequently, the scaled dataset is mean-centered. Mathematically, mean-centering means that adding up the values of the individual elements of column i of a data matrix results in zero for column i. This is achieved by subtracting the mean of column from all values of the individual elements of column i.

PLS Analysis

PLS analysis (Geladi and Kowalski, 1986) was performed in the Matlab environment using the PLS Toolbox (version 3.5.4, 2006; Eigenvector Research, Manson, Wash.).

It is possible that transcripts that show a lot of variation disturb the performance of the PLS model. Therefore, the model was optimized using a jack-knife approach. A model was build leaving out 10% of the samples, which was repeated until all samples were left out once. For each transcript, the relative standard deviation (RSD) was calculated and transcripts which had an RSD>50% were left out to build a second PLS model.

Validation of the Results

A double cross-validation procedure was used to validate the PLS model. In short, two loops are defined: an inner loop and an outer loop. In the innerloop 90% of the data is used to find an optimal PLS model. In the outerloop a prediction is made for the remaining 10% of the data based on the innerloop PLS model. This is repeated until all samples are left out once (so in this case 10 times). Goal of the DCV is to get an independent estimate of the prediction error. The $R^2$ was calculated to determine how good the original productivity or titer was predicted by the model. The closer the $R^2$ gets to 1, the better the model.

Sequence Analysis of Spots Selected after Transcriptomics Approach

The relevant clones were selected from the glycerol stocks of the ordered libraries (gDNA and cDNA library respectively) and cultivated in 96-well microtiter plates. The sequences of the inserts from both the 3' and the 5' end were determined by High Throuput (HT) sequencing service.

All RNA samples were labelled with Cy5. Hybridisations were performed with all 30 RNA samples, using Cy3-labeled chromosomal DNA of *A. terreus* as the reference.

The raw transcriptomics data were shown to be of high quality, based on visual inspection of the arrays after fluorescence scanning. Notably, also the hybridization with the partially degraded RNA samples gave good results.

The normalized data were subsequently combined. As the *A. terreus* array consisted out of two slides, different strategies of combining the data from the two slides were pursued, making use of the fact that the cDNA clones are present on both the A and B slide:

SET 1=mean expression signal of the cDNA clones on slide A and B, take only those spots that give a signal on both the A and B slide SET 2=use only the signal of the cDNA spots on the A slide. Spots with a Signal/Background below 1.5 were removed.

SET 3=use only the signal of the cDNA spots on the B slide. Spots with a Signal/Background below 1.5 were removed.

SET 4=Combimean cDNA data of both the A and B slide;
  i. If both measurement values were zero the combined value was zero;
  ii. If both measurements values were both non-zero, the combined value was equal to the average of the two measurement values;
  iii. If one of the two measurement values was zero and the other measurement value was non-zero, the combined value was equal to the non-zero measurement value.

SET 5=SET 1+normalized gDNA spots using the normalization factor calculated based on the cDNA clones.

The most relevant spots were subsequently identified by multivariate regression analysis, Multivariate data analysis (MVDA) tools seem very well suited to prioritize leads from functional genomics datasets. These tools take into account the inherent interdependency of biomolecules. These tools allow the identification of the specific genes that are the most important for a specific phenotype by determining the strength of the correlation of the expression of every gene with the biological question under study. Especially the regression tool partial least squares (PLS) holds great promise. Principally, the application of PLS results in a model (equation) that predicts a quantifiable phenotype of interest (e.g. itaconic acid titer, P) in terms of the transcripts (A, B, C, . . . ) expressed in *A. terreus*;

$$P=b_1A+b_2B+b_3C+\ldots$$

By subsequently ordering the transcripts based on the absolute value of the regression values (i.e. $b_1$, $b_2$, $b_3$, . . . ) transcripts are identified that contribute the most to itaconate production.

PLS models with both the itaconate titers of the different samples and the itaconate productivity of the different samples were built using these different combined data sets. Moreover, not only linear models but also logarithmic models were built using the log of the itaconate titer (Table 4). Of these, only the (linear) itaconate titer models were reasonably good models as judged by the (double) cross validation results and the stability of these models (i.e. $R^2$ double cross validation≈0.4-0.5)(Table 4). The results of the other PLS models were very poor, and these models were not pursued.

TABLE 4

Overview of the PLS models build using the transcriptomics data set

| X (data set) | Y (Phenotype) | $R^2$ double cross validation PLS model |
|---|---|---|
| SET 1 | Productivity | 0.10 |
|  | Titer | 0.51 |
|  | Log(titer) | 0.05 |
| SET 2 | Productivity | 0.13 |
|  | Titer | 0.41 |
|  | Log(titer) | 0.18 |
| SET 3 | Productivity | 0.08 |
|  | Titer | 0.45 |
|  | Log(titer) | 0.06 |
| SET 4 | Productivity | 0.07 |
|  | Titer | 0.40 |
|  | Log(titer) | 0.12 |
| SET 5 | Productivity | 0.08 |
|  | Titer | 0.38 |
|  | Log(titer) | 0.05 |

Moreover, a second PLS model was built with the titer as the Y-variable, using only the transcripts whose regression value had an RSD<50% (as determined based on jack-knifing) in the first PLS model. This were, in general, only some 10-20% of the spots of the complete data set.

'Top 20'-ies of the combined data data sets analyzed by PLS using the itaconic acid titer as the phenotype were generated. These 'top-20'-ies were combined, and unique spots were identified (Table 5 and 6). In total 102 of the most relevant spots obtained after PLS analyses (based on 10 models; 5 data sets, 2 PLS models per data set) were selected for sequencing.

Of the selected spots, >92% were spots belonging to cDNA clones. However, also four of the 5 combined data sets contained only cDNA clones (see above).

Following sequence analysis of the 102 selected spots, the genes present on these inserts were identified by performing a homology search using BLAST based on the draft version of the *A. terreus* genome sequence as available from the BROAD institute (http://www.broad.mit.edu/annotation/fgi/).

As different combined data sets/'top 20'-ies were generated, the overall ranking of the transcripts, as reported in Table 5 was based on:

(i) The frequency of occurrence of an individual spot in the top 20 of the different combined data sets analyzed
(ii) The sum of the overall rank of a spot in the different 'top 20'-ies of the different combined data sets.

Table 5 shows the results of the genes identified on the 20 highest overall ranking spots identified by PLS analysis based on titer.

TABLE 5

Overall Top 20 PLS analysis - itaconic acid titer.

| Rank | Clone ID | Gene locus | Gene name |
|---|---|---|---|
| 1 | AsTeR010H08 | | |
| 2 | AsTeR037H12 | | |
| 3 | AsTeR053F06 | | |
| 4 | AsTeR037C07 | | |
| 5 | AsTeR007H08 | | |
| 6 | AsTeR048G12 | | |
| 7 | AsTeR023B07 | | |
| 8 | AsTeR033F08 | | |
| 9 | AsTeR035E10 | | |
| 10 | AsTeR033A04 | | |
| 11 | AsTeR029F07 | | |
| 12 | AsTeR045A05 | | |
| 13 | AsTeR010H12 | | |
| 14 | AsTeR041C10 | | |
| 15 | AsTeR030D01 | ATEG_09972.1 | Predicted protein |
| 16 | AsTeR009D10 | | |
| 17 | AsTeR032E02 | | |
| 18 | AsTeR032H04 | | |
| 19 | AsTeR004H04 | | |
| 20 | AsTeR054B06 | | |

Moreover, a ranked list of the genes that were identified with the highest frequency amongst the in total 190 clones sequenced (i.e. 102 spots selected after PLS analyses and 88 spots obtained after the differential analyses—See EP 08151584)(Table 6).

TABLE 6

Most frequently identified genes amongst the 190 clones sequenced

| Freq. | Gene locus | # clones from differential approach | # clones from PLS approach | Regulation under itaconate producing conditions | Gene name |
|---|---|---|---|---|---|
| 25 | ATEG_09970.1 | 25 | | Up | mitochondrial tricarboxylic acid transporter - EP08151584 |
| 19 | | | | | |
| 15 | ATEG_09971.1 | 14 | 1 | Up | cis-aconitate decarboxylase (EP 07112895) |
| 14 | | | | | |
| 11 | | | | | |
| 7 | | | | | |
| 7 | | | | | |
| 4 | | | | | |
| 3 | | | | | |
| 3 | | | | | |
| 2 | ATEG_09972.1 | | 2 | Up | Predicted protein |
| 2 | | | | | |
| 2 | | | | | |
| 2 | | | | | |
| 2 | | | | | |
| 2 | | | | | |
| 2 | | | | | |
| 2 | | | | | |
| 2 | | | | | |

The ATEG_00972.1 gene, flanking cis-aconitate decarboxylase (ATEG_09971.1 - EP 07112895), and the putative mitochondrial tricarboxylate transporter protein (ATEG_09970.1 - EP08151584) were identified on two of the spots identified by PLS analysis (Table 6) and had an overall rank of 15 in the combined top 20 (Table 5). Just as the CAD gene and the MTAT gene, the ATEG_09972.1 gene, was found to be upregulated under itaconic acid producing environmental conditions.

Example 4

Homology Analysis of the ATEG_09972.1 Gene

A BLAST search was performed in order to identify homologous to the predicted protein ATEG_09972.1 (Table 7). High homologies were only found with genes from two other *A. terreus* strains. With other micro-organisms and more specifically fungi, homologues were found although with a relatively low homology. Based on the annotation of these homologous genes and the major facilitator superfamily domain identified in this gene, ATEG_09972.1 was identified as an itaconate exporter.

TABLE 7

BLAST search results with ATEG_09972.1

| Rank | Protein | Best Hit | E value | Identity/Similarity |
|---|---|---|---|---|
| 1 | Predicted protein | XP_001209274.1 *A. terreus* | 0.0 | 100%/100% |
| 2 | unknown | AAD34564.1 *A. terreus* | 0.0 | 92%/93% |
| 3 | Unnamed protein product | BAE57135.1 *A. oryzae* | 2e−160 | 70%/84% |
| 4 | putitative MFS transporter | XP_749665.1 *A. fumigatus* | 5e−135 | 64%/77% |
| 5 | putitative MFS transporter | XP_001260160.1 *N. fischeri* | 5e−134 | 65%/79% |
| 6 | Hypothetical protein AN7512.2 | XP_680781.1 *A. nidulans* | 5e−123 | 59%/74% |
| 7 | Hypothetical protein AN6019.2 | XP_663623.1 *A. nidulans* | 1e−105 | 52%/68% |
| 8 | Unnamed protein product | BAE61268.1 *A. oryzae* | 1e−91 | 45%/61% |
| 9 | pH-responsive protein 2 precursor | XP_001215904.1 *A. terreus* | 2e−91 | 68%/81% |
| 10 | hypothetical protein Fgo2824.1 | XP_383000.1 *G. zeae* | 1e−81 | 47%/63% |

It appears that at least the gene coding for the cis-aconitate decarboxylase (ATEG_09971.1) and the gene encoding the mitochondrial tricarboxylate transporter (ATEG_9970.1) lie in the same cluster in the *A. terreus* genome (FIG. 2).

A gene neighbouring CAD, the mitochondrial tricarboxylate transporter and the itaconate exporter is a putative regulator containing a zinc-finger domain (ATEG_09969.1). This gene was not identified using our transcriptomics approach, but considering its localization it is expected that it is relevant for itaconic acid synthesis FIG. 2 shows that also the lovastatin pathway genes are located on this cluster, suggesting a link between both pathways which are (mainly) specific for *A. terreus*.

Example 5

(Co-)Expression of the ATEG_09972.1 Gene in *Aspergillus Niger*

In order to unambiguously establish that the ATEG_09972.1 protein aids to the increased production of itaconic acid, a naturally non-itaconic acid producing fungal host was (co-)transformed with the CAD gene or transformed with the CAD and MTT (ATEG_09970.1) gene were co-transformed with the ATEG_09972.1 (MFS) gene.

Expression of the CAD (ATEG 09971.1) Gene in *Aspergillus Niger*

A PCR generated copy of the gene encoding the CAD protein (see EP07112895) was generated. For this purpose two sets of primers were generated as shown below. PCR amplification based on *A. terreus* NRRL1960 genomic DNA resulted in the isolation of PCR fragments from which the complete coding region of the gene encoding the CAD protein, could be isolated as BspHI-BamHI fragments.

```
CAD full sequence 1529 bp (SEQ ID NO: 11)
ORIGIN

BspHI   cadfor40° C.
  5'-ATCGTCATGACCAAGCAATCTG-3'  (SEQ ID NO: 7)

BspHI   cadfor53° C.
  5'-ATCGTCATGACCAAGCAATCTGCGGACA-3'  (SEQ ID NO: 8)

1 ATGACCAAGC AATCTGCGGA CAGCAACGCA AAGTCAGGAG TTACGTCCGA AATATGTCAT

61 TGGGCATCCA ACCTGGCCAC TGACGACATC CCTTCGGACG TATTAGAAAG AGCAAAATAC

121 CTTATTCTCG ACGGTATTGC ATGTGCCTGG GTTGGTGCAA GAGTGCCTTG GTCAGAGAAG

181 TATGTTCAGG CAACGATGAG CTTTGAGCCG CCGGGGGCCT GCAGGGTGAT TGGATATGGA

241 CAGgtaaatt ttattcactc tagacggtcc acaaagtata ctgacgatcc ttcgtatagA
                                  (intron)

301 AACTGGGGCC TGTTGCAGCA GCCATGACCA ATTCCGCTTT CATACAGGCT ACGGAGCTTG

361 ACGACTACCA CAGCGAAGCC CCCTACACT CTGCAAGCAT TGTCCTTCCT GCGGTCTTTG

421 CAGCAAGTGA GGTCTTAGCC GAGCAGGGCA AAACAATTTC CGGTATAGAT GTTATTCTAG

481 CCGCCATTGT GGGGTTTGAA TCTGGCCCAC GGATCGGCAA AGCAATCTAC GGATCGGACC

541 TCTTGAACAA CGGCTGGCAT TGTGGAGCTG TGTATGGCGC TCCAGCCGGT GCGCTGGCCA

601 CAGGAAAGCT CTTCGGTCTA ACTCCAGACT CCATGGAAGA TGCTCTCGGA ATTGCGTGCA

661 CGCAAGCCTG TGGTTTAATG TCGGCGCAAT ACGGAGGCAT GGTAAAGCGT GTGCAACACG
```

```
-continued
 721  GATTCGCAGC GCGTAATGGT CTTCTTGGGG GACTGTTGGC CCATGGTGGG TACGAGGCAA

781  TGAAAGGTGT CCTGGAGAGA TCTTACGGCG GTTTCCTCAA GATGTTCACC AAGGGCAACG

841  GCAGAGAGCC TCCCTACAAA GAGGAGGAAG TGGTGGCTGG TCTCGGTTCA TTCTGGCATA

901  CCTTTACTAT TCGCATCAAG CTCTATGCCT GCTGCGGACT TGTCCATGGT CCAGTCGAGG

961  CTATCGAAAA CCTTCAGGGG AGATACCCCG AGCTCTTGAA TAGAGCCAAC CTCAGCAACA

1021  TTCGCCATGT TCATGTACAG CTTTCAACGG CTTCGAACAG TCACTGTGGA TGGATACCAG

1081  AGGAGAGACC CATCAGTTCA ATCGCAGGGC AGATGAGTGT CGCATACATT CTCGCCGTCC

1141  AGCTGGTCGA CCAGCAATGT CTTTTGTCCC AGTTTTCTGA GTTTGATGAC AACCTGGAGA

1201  GGCCAGAAGT TTGGGATCTG GCCAGGAAGG TTACTTCATC TCAAAGCGAA GAGTTTGATC

1261  AAGACGGCAA CTGTCTCAGT GCGGGTCGCG TGAGGATTGA GTTCAACGAT GGTTCTTCTA

1321  TTACGGAAAG TGTCGAGAAG CCTCTTGGTG TCAAAGAGCC CATGCCAAAC GAACGGATTC

1381  TCCACAAATA CCGAACCCTT GCTGGTAGCG TGACGGACGA ATCCCGGGTG AAAGAGATTG

1441  AGGATCTTGT CCTCGGCCTG GACAGGCTCA CCGACATTAG CCCATTGCTG GAGCTGCTGA

1501  ATTGCCCCGT AAAATCGCCA CTGGTATAA
```

```
                cadrev42° C.         BamHI
      3'-TTTAGCGGTGACCATATTCCTAGGCCCT-5'  (SEQ ID NO: 9)

cadrev52° C.         BamHI
      3'-GGCA TTTAGCGGTGACCATATTCCTAGGCCCC-5'  (SEQ ID NO: 10)
```

Translation of CAD encoding gene (SEQ ID NO: 12)
Total amino acid number: 490, MW=52710

```
  1   M T K Q S A D S N A K S G V T S E I C H
 21   W A S N L A T D D I P S D V L E R A K Y
 41   L I L D G I A C A W V G A R V P W S E K
 61   Y V Q A T M S F E P P G A C R V I G Y G
 81   Q K L G P V A A A M T N S A F I Q A T E
101   L D D Y H S E A P L H S A S I V L P A V
121   F A A S E V L A E Q G K T I S G I D V I
141   L A A I V G F E S G P R I G K A I Y G S
161   D L L N N G W H C G A V Y G A P A G A L
181   A T G K L F G L T P D S M E D A L G I A
201   C T Q A C G L M S A Q Y G G M V K R V Q
221   H G F A A R N G L L G G L L A H G G Y E
241   A M K G V L E R S Y G G F L K M F T K G
261   N G R E P P Y K E E E V V A G L G S F W
281   H T F T I R I K L Y A C C G L V H G P V
301   E A I E N L Q G R Y P E L L N R A N L S
321   N I R H V H V Q L S T A S N S H C G W I
341   P E E R P I S S I A G Q M S V A Y I L A
361   V Q L V D Q Q C L L S Q F S E F D D N L
381   E R P E V W D L A R K V T S S Q S E E F
401   D Q D G N C L S A G R V R I E F N D G S
421   S I T E S V E K P L G V K E P M P N E R
441   I L H K Y R T L A G S V T D E S R V K E
461   I E D L V L G L D R L T D I S P L L E L
481   L N C P V K S P L V *
```

The resulting BspHI-BamHI fragment was cloned into the *Aspergillus* expression vector pAN52-4-amdS derived from *Aspergillus* expression vector pAN52-4. The *Aspergillus* expression vector pAN52-4-amdS was derived by cloning the *Aspergillus* selection marker amdS into the *Aspergillus* expression vector pAN52-4 (EMBL accession #Z32699).

Subsequently, an *Aspergillus niger* strain AB1.13 (Mattern, I. E. et al., 1992, Mol. Gen. Genet. 234:332-336) was transformed with the CAD expression vector. AmdS transformants resulting for this experiment were purified by single colony purification and retested for their AmdS+ phenotype.

Co-Expression of the CAD Gene and the ATEG 09970.1 Gene in *Aspergillus Niger*

The ATEG_09970.1 gene (MTT) was synthesized (GeneArt) and cloned into *Aspergillus niger* expression vector pAN52-5doubleNotI by restriction enzyme cutting sites of double NotI. The expression vector pAN52-5doubleNotI was derived by adding an extra NotI site in the *Aspergillus* expression vector pAN52-4 (EMBL accession #Z32699). Moreover, the codons of the clone were optimized for expression in the *Aspergillus niger* strain.

Translation of MTT cds (1-861) (SEQ ID NOS:13-14)
Universal code
Total amino acid number: 286, MW=31503
Max ORF starts at AA pos 1 (may be DNA pos 1) for 286 AA (858 bases), MW=31503

```
  1 ATGAGTATTCAACATTTCCGTGTCGCCCTTATTCCCTTTTTTGCGGCATTTTGCCTTCCT
  1 M  S  I  Q  H  F  R  V  A  L  I  P  F  F  A  A  F  C  L  P

61 GTTTTTGCTCACCCAGAAACGCTGGTGAAAGTAAAAGATGCTGAAGATCAGTTGGGTGCA
 21 V  F  A  H  P  E  T  L  V  K  V  K  D  A  E  D  Q  L  G  A

121 CGAGTGGGTTACATCGAACTGGATCTCAACAGCGGTAAGATCCTTGAGAGTTTTCGCCCC
 41 R  V  G  Y  I  E  L  D  L  N  S  G  K  I  L  E  S  F  R  P

181 GAAGAACGTTTTCCAATGATGAGCACTTTTAAAGTTCTGCTATGTGGCGCGGTATTATCC
 61 E  E  R  F  P  M  M  S  T  F  K  V  L  L  C  G  A  V  L  S

241 CGTATTGACGCCGGGCAAGAGCAACTCGGTCGCCGCATACACTATTCTCAGAATGACTTG
 81 R  I  D  A  G  Q  E  Q  L  G  R  R  I  H  Y  S  Q  N  D  L

301 GTTGAGTACTCACCAGTCACAGAAAAGCATCTTACGGATGGCATGACAGTAAGAGAATTA
101 V  E  Y  S  P  V  T  E  K  H  L  T  D  G  M  T  V  R  E  L

361 TGCAGTGCTGCCATAACCATGAGTGATAACACTGCGGCCAACTTACTTCTGACAACGATC
121 C  S  A  A  I  T  M  S  D  N  T  A  A  N  L  L  L  T  T  I

421 GGAGGACCGAAGGAGCTAACCGCTTTTTTGCACAACATGGGGGATCATGTAACTCGCCTT
141 G  G  P  K  E  L  T  A  F  L  H  N  M  G  D  H  V  T  R  L

481 GATCGTTGGGAACCGGAGCTGAATGAAGCCATACCAAACGACGAGCGTGACACCACGATG
161 D  R  W  E  P  E  L  N  E  A  I  P  N  D  E  R  D  T  T  M

541 CCTGTAGCAATGGCAACAACGTTGCGCAAACTATTAACTGGCGAACTACTTACTCTAGCT
181 P  V  A  M  A  T  T  L  R  K  L  L  T  G  E  L  L  T  L  A

601 TCCCGGCAACAATTAATAGACTGGATGGAGGCGGATAAAGTTGCAGGACCACTTCTGCGC
201 S  R  Q  Q  L  I  D  W  M  E  A  D  K  V  A  G  P  L  L  R

661 TCGGCCCTTCCGGCTGGCTGGTTTATTGCTGATAAATCTGGAGCCGGTGAGCGTGGGTCT
221 S  A  L  P  A  G  W  F  I  A  D  K  S  G  A  G  E  R  G  S

721 CGCGGTATCATTGCAGCACTGGGGCCAGATGGTAAGCCCTCCCGTATCGTAGTTATCTAC
241 R  G  I  I  A  A  L  G  P  D  G  K  P  S  R  I  V  V  I  Y

781 ACGACGGGGAGTCAGGCAACTATGGATGAACGAAATAGACAGATCGCTGAGATAGGTGCC
261 T  T  G  S  Q  A  T  M  D  E  R  N  R  Q  I  A  E  I  G  A

841 TCACTGATTAAGCATTGGTAA
281 S  L  I  K  H  W  *
```

Subsequently, an *Aspergillus niger* strain AB1.13 (Mattern, I. E. et al., 1992, Mol. Gen. Genet. 234:332-336) was co-transformed with the CAD expression vector and the MTT expression vector. AmdS transformants resulting for this experiment were purified by single colony purification and retested for their AmdS+ phenotype.

Co-Expression of the Cad Gene, MTT Gene (ATEG 09970.1) Together with the ATEG-09972.1 Gene in *Aspergillus Niger*

The ATEG-09972.1 (MFS) gene was synthesized (GeneArt) and cloned into *Aspergillus niger* expression vector pAN52-5doubleNotI by restriction enzyme cutting sites of double NotI. The expression vector pAN52-5doubleNotI was derived by adding an extra NotI site in the *Aspergillus* expression vector pAN52-4 (EMBL accession #Z32699). Moreover, codons of the clone were optimized for expression in the *Aspergillus niger* strain.

Translation of MFS cds (1-861) (SEQ ID NOS:15-16)

Universal code

Total amino acid number: 286, MW=31503

Max ORF starts at AA pos 1 (may be DNA pos 1) for 286 AA 9858 bases), MW=31503

```
  1 ATGAGTATTCAACATTTCCGTGTCGCCCTTATTCCCTTTTTTGCGGCATTTTGCCTTCCT
  1 M  S  I  Q  H  F  R  V  A  L  I  P  F  F  A  A  F  C  L  P

61 GTTTTTGCTCACCCAGAAACGCTGGTGAAAGTAAAAGATGCTGAAGATCAGTTGGGTGCA
 21 V  F  A  H  P  E  T  L  V  K  V  K  D  A  E  D  Q  L  G  A

121 CGAGTGGGTTACATCGAACTGGATCTCAACAGCGGTAAGATCCTTGAGAGTTTTCGCCCC
 41 R  V  G  Y  I  E  L  D  L  N  S  G  K  I  L  E  S  F  R  P

181 GAAGAACGTTTTCCAATGATGAGCACTTTTAAAGTTCTGCTATGTGGCGCGGTATTATCC
 61 E  E  R  F  P  M  M  S  T  F  K  V  L  L  C  G  A  V  L  S

241 CGTATTGACGCCGGGCAAGAGCAACTCGGTCGCCGCATACACTATTCTCAGAATGACTTG
 81 R  I  D  A  G  Q  E  Q  L  G  R  R  I  H  Y  S  Q  N  D  L

301 GTTGAGTACTCACCAGTCACAGAAAAGCATCTTACGGATGGCATGACAGTAAGAGAATTA
101 V  E  Y  S  P  V  T  E  K  H  L  T  D  G  M  T  V  R  E  L

361 TGCAGTGCTGCCATAACCATGAGTGATAACACTGCGGCCAACTTACTTCTGACAACGATC
```

```
-continued
121 C  S  A  A  I  T  M  S  D  N  T  A  A  N  L  L  L  T  T  I

421 GGAGGACCGAAGGAGCTAACCGCTTTTTTGCACAACATGGGGGATCATGTAACTCGCCTT
141 G  G  P  K  E  L  T  A  F  L  H  N  M  G  D  H  V  T  R  L

481 GATCGTTGGGAACCGGAGCTGAATGAAGCCATACCAAACGACGAGCGTGACACCACGATG
161 D  R  W  E  P  E  L  N  E  A  I  P  N  D  E  R  D  T  T  M

541 CCTGTAGCAATGGCAACAACGTTGCGCAAACTATTAACTGGCGAACTACTTACTCTAGCT
181 P  V  A  M  A  T  T  L  R  K  L  L  T  G  E  L  L  T  L  A

601 TCCCGGCAACAATTAATAGACTGGATGGAGGCGGATAAAGTTGCAGGACCACTTCTGCGC
201 S  R  Q  Q  L  I  D  W  M  E  A  D  K  V  A  G  P  L  L  R

661 TCGGCCCTTCCGGCTGGCTGGTTTATTGCTGATAAATCTGGAGCCGGTGAGCGTGGGTCT
221 S  A  L  P  A  G  W  F  I  A  D  K  S  G  A  G  E  R  G  S

721 CGCGGTATCATTGCAGCACTGGGGCCAGATGGTAAGCCCTCCCGTATCGTAGTTATCTAC
241 R  G  I  I  A  A  L  G  P  D  G  K  P  S  R  I  V  V  I  Y

781 ACGACGGGGAGTCAGGCAACTATGGATGAACGAAATAGACAGATCGCTGAGATAGGTGCC
261 T  T  G  S  Q  A  T  M  D  E  R  N  R  Q  I  A  E  I  G  A

841 TCACTGATTAAGCATTGGTAA
281 S  L  I  K  H  W  *
```

Subsequently, an *Aspergillus niger* strain AB1.13 (Mattern, I. E. et al., 1992, Mol. Gen. Genet. 234:332-336) was co-transformed with the CAD expression vector, the MTT expression vector and the MFS expression vector. AmdS transformants resulting for this experiment were purified by single colony purification and retested for their AmdS+ phenotype.

Analysis of *A. Niger* Transformants for Itaconic Acid Production

Several positive transformants and the parental host strain were subsequently cultured in Shake Flask in MM medium supplied with uridine containing glucose as C-source and nitrate as N-source. Medium samples from the various cultures were analyzed by HPLC for the presence of itaconic acid (Table 8).

Shake Flask Medium Compositions:

Per liter: 0.52 g of KCl, 2.4 g of NaNO$_3$, 1.56 g of KH$_2$PO$_4$, 0.24 g of MgSO$_4$*7H$_2$O, 5 mg of Fe(III) SO$_4$*7H$_2$O, 5 mg of MnCl$_2$*4H$_2$O, 0.022 g of ZnSO$_4$*7H$_2$O, 0.011 g of H$_3$BO$_3$, 1.7 mg of CoCl$_2$*6H$_2$O and 2.44 g of uridine, 100 g of glucose as a carbon source. All media were prepared in demineralised water.

HPLC analysis was performed with a reversed phase column, using a Develosil™ 3 μm R$^P$-Aqueous C30 140A column at a constant temperature of 25° C., with elution with 20 mM NaH2PO4, pH 2.25 and acetonitril. Compounds were detected by UV at 210 nm using a Waters 2487 Dual wavelength Absorbance detector (Milford, Mass., USA). Retention time of itaconic acid was 18.82 min.

TABLE 8

Itaconic acid concentration in the culture fluid of the *A. niger* AB1.13 transformants cultivated in shake flasks.

*Aspergillus niger* AB 1.13 transformants (AB 1.13 CAD)

| strain | code | time (hrs) | itaconic acid mg/g wet weight |
|---|---|---|---|
| AB 1.13 | WT | 54 | 0 |
| AB 1.13 CAD | 5.1 | 54 | 1.0 |
| AB 1.13 CAD | 7.2 | 54 | 0.7 |
| AB 1.13 CAD | 10.1 | 54 | 1.4 |
| AB 1.13 CAD | 14.2 | 54 | 1.2 |
| AB 1.13 CAD | 16.1 | 54 | 1.2 |
| AB 1.13 CAD + MTT | 4.1 | 54 | 1.3 |

TABLE 8-continued

Itaconic acid concentration in the culture fluid of the *A. niger* AB1.13 transformants cultivated in shake flasks.

*Aspergillus niger* AB 1.13 transformants (AB 1.13 CAD)

| strain | code | time (hrs) | itaconic acid mg/g wet weight |
|---|---|---|---|
| AB 1.13 CAD + MTT | 6.2 | 54 | 1.5 |
| AB 1.13 CAD + MTT | 2.2.1 | 54 | 2.2 |
| AB 1.13 CAD + MTT + MFS | 9.2.1* | 54 | 2.3 |
| AB 1.13 CAD + MTT + MFS | 9.2.2* | 54 | 2.5 |
| AB 1.13 CAD + MTT + MFS | 9.4.1* | 54 | 2.5 |
| AB 1.13 CAD + MTT + MFS | 12.1.1 | 54 | 2.3 |

*Duplicate isolates of the same transformant.

No itaconic acid was detected in the supernatant of the parental strain while in the culture fluid of the strains containing the CAD gene (strains marked CAD), itaconic acid was detected.

In both the culture fluid of the strains containing the CAD gene and the strains containing both the CAD gene and MTT gene (strains marked CAD+MTT) and the strains containing the CAD, the MTT and the MFS gene (strains marked CAD+MTT+MFS), itaconic acid was detected (Table 8). In all MFS expressing strains more itaconic acid was produced in the culture fluid than in the strains expressing only the CAD gene, or the CAD and the MTT gene. Moreover, the average itaconic acid concentration was higher in the culture fluid of the strains expressing the MFS, the CAD and the MTT gene compared to the transformants expressing only the CAD or the CAD+MTT gene: 2.4 mg itaconic acid/g mycelial wet weight versus 1.1 mg itaconic acid/g mycelial wet weight (CAD gene only) and 1.7 mg itaconic acid/g mycelial wet weight (CAD+MTT gene—Table 8).

The invention claimed is:

1. A method for enhancing the production of itaconic acid in a micro-organism that is capable of producing itaconic acid said method comprising increasing the activity of an itaconate transporter protein in said microorganism, wherein the increasing is effected by expressing a nucleotide sequence encoding said itaconate transporter protein
wherein the itaconate transporter protein has the amino acid sequence of SEQ ID NO:3 or an amino acid sequence at least 95% identical thereto or SEQ ID NO:6, and
culturing said microorganism under conditions whereby itaconic acid is produced.

2. The method of claim 1, wherein the nucleotide sequence encodes a protein having SEQ ID NO:3 or SEQ ID NO:6.

3. The method of claim 1, wherein the micro-organism is a citrate producing micro-organism.

4. The method of claim 1, wherein the micro-organism is a lovastatin producing micro-organism.

5. The method of claim 1, wherein the expressing is effected by providing a vector comprising a promoter operably linked to said nucleotide sequence.

6. The method of claim 1, further comprising isolating itaconic acid from the extracellular medium.

7. The method of claim 3 wherein the citrate producing microorganism is *A. terreus, A. niger, A. itaconicus, A. nidulans, A. oryzae, A. fumigates, Yarrowia lipolytica, Ustilago zeae, Candida* sp., *Rhodotorula* sp., *Pseudozyma antarctica, E. coli,* or *Saccharomyces cerevisiae.*

8. The method of claim 4 wherein the lovastatin producing microorganism is *Monascus* spp., *Penicillium* spp., *Hypomyces* spp., *Doratomyces* spp., *Phoma* spp., *Eupenicillium* spp., *Gymnoascus* spp., *Pichia labacensis, Candida cariosilognicola, Paecilomyces variotii, Scopulariopsis brevicaulis* or *Trichoderma* spp.

9. The method of claim 1 wherein the nucleotide sequence comprises SEQ ID NO:2 or a nucleotide sequence at least 95% identical thereto or SEQ ID NO:5.

10. The method of claim 1 wherein the nucleotide sequence comprises SEQ ID NO:2 or SEQ ID NO:5.

* * * * *

UNITED STATES PATENT AND TRADEMARK OFFICE
CERTIFICATE OF CORRECTION

PATENT NO.       : 8,642,298 B2                                      Page 1 of 1
APPLICATION NO.  : 12/920461
DATED            : February 4, 2014
INVENTOR(S)      : Van Der Werf et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 430 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 14

<210> SEQ ID NO 1
<211> LENGTH: 1392
<212> TYPE: DNA
<213> ORGANISM: Aspergillus terreus

<400> SEQUENCE: 1

```
atgggccacg gtgacactga gtccccgaac ccaacgacga ccacggaagg tagcggacaa      60
aacgagccag agaaaaaggg ccgtgatatt ccattatgga gaaaatgtgt cattacgttt     120
gttgttagtt ggatgactct agtcgttact ttctccagta cttgtcttct tcctgccgcc     180
cctgaaatcg cgaatgaatt tgatatgact gtcgagacta tcaacatctc caatgctggt     240
gtcctagttg ccatgggata ttcatccctc atatgggtc ccatgaacaa gttagtcggc     300
cggcggacat catacaatct ggccatttca atgctttgtg catgctccgc tggaacggca     360
gcggcgataa acgaggaaat gttcatagcg ttcagagtgt tgagcggctt aaccggaacc     420
tcgttcatgg tctcaggcca aactgttctt gcagatatct ttgagcctgt acgaatcaca     480
cgccctcgtc tccccaattg cgaaaactaa tccgttcgtg cgcaggttta ccgtgggacg     540
gccgtaggtt tcttcatggc cgggactctt tctggccctg caataggtac gtaccctgct     600
gcaagtacta gaactcccaa caggaactaa ttgtatgagc aggcccctgc gtgggagggg     660
tcatcgtcac tttcacgagt tggcgtgtta tcttctggct tcaactaggt atgagcgggc     720
tggggctcgt gctttctctg ctatttttcc cgaaaatcga aggaaattct gagaaggtct     780
caacggcgtt taaaccgacc acacttgtca caatcatatc gaaattctcc ccaacggatg     840
tgctcaagca gtgggtgtat ccaaatgtct ttcttgccgt aagtgtctgg acatatacc     900
ctctgcatct actggaaaac gagatgctca tgccacaaat caaaggactt atgctgtggc     960
ctcctggcaa tcacgcaata ttcgatcctg acttcagctc gtgccatatt caactcacga    1020
tttcatttaa cgactgccct agtatcgggt ctcttctacc tcgctccagg tgccgggttc    1080
ctgataggca gtctcgtcgg cggtaaactt tcggatcgca ccgttcggag atacatagta    1140
aagcgcggat ccgtctcccc tcaggatcga ctccacagcg ggctcatcac attgttcgcc    1200
gtgctgcccg caggaacgct catttacggg tggacactcc aagaggataa gggtgatatg    1260
gtagtgccca taatcgcggc gttcttcgcg ggctgggggc tcatgggcag ttttaactgc    1320
ctgaacactt acgtgctggg tttgttccac accctcattt atctattccc tttgtgtaca    1380
tgcccacaat aa                                                        1392
```

<210> SEQ ID NO 2
<211> LENGTH: 1212
<212> TYPE: DNA
<213> ORGANISM: Aspergillus terreus
<220> FEATURE:
<221> NAME/KEY: CDS
<222> LOCATION: (1)..(1212)

<400> SEQUENCE: 2

```
atg ggc cac ggt gac act gag tcc ccg aac cca acg acg acc acg gaa       48
Met Gly His Gly Asp Thr Glu Ser Pro Asn Pro Thr Thr Thr Thr Glu
1               5                   10                  15 ggt agc gga caa aac gag cca gag aaa aag ggc cgt gat att cca tta       96
Gly Ser Gly Gln Asn Glu Pro Glu Lys Lys Gly Arg Asp Ile Pro Leu
            20                  25                  30 tgg aga aaa tgt gtc att acg ttt gtt gtt agt tgg atg act cta gtc      144
```

```
Trp Arg Lys Cys Val Ile Thr Phe Val Val Ser Trp Met Thr Leu Val
        35                  40                  45 gtt act ttc tcc agt act tgt ctt ctt cct gcc gcc cct gaa atc gcg      192
Val Thr Phe Ser Ser Thr Cys Leu Leu Pro Ala Ala Pro Glu Ile Ala
 50                  55                  60 aat gaa ttt gat atg act gtc gag act atc aac atc tcc aat gct ggt      240
Asn Glu Phe Asp Met Thr Val Glu Thr Ile Asn Ile Ser Asn Ala Gly
 65                  70                  75                  80 gtc cta gtt gcc atg gga tat tca tcc ctc ata tgg ggt ccc atg aac      288
Val Leu Val Ala Met Gly Tyr Ser Ser Leu Ile Trp Gly Pro Met Asn
                 85                  90                  95 aag tta gtc ggc cgg cgg aca tca tac aat ctg gcc att tca atg ctt      336
Lys Leu Val Gly Arg Arg Thr Ser Tyr Asn Leu Ala Ile Ser Met Leu
             100                 105                 110 tgt gca tgc tcc gct gga acg gca gcg gcg ata aac gag gaa atg ttc      384
Cys Ala Cys Ser Ala Gly Thr Ala Ala Ala Ile Asn Glu Glu Met Phe
             115                 120                 125 ata gcg ttc aga gtg ttg agc ggc tta acc gga acc tcg ttc atg gtc      432
Ile Ala Phe Arg Val Leu Ser Gly Leu Thr Gly Thr Ser Phe Met Val
130                 135                 140 tca ggc caa act gtt ctt gca gat atc ttt gag cct gtt tac cgt ggg      480
Ser Gly Gln Thr Val Leu Ala Asp Ile Phe Glu Pro Val Tyr Arg Gly
145                 150                 155                 160 acg gcc gta ggt ttc ttc atg gcc ggg act ctt tct ggc cct gca ata      528
Thr Ala Val Gly Phe Phe Met Ala Gly Thr Leu Ser Gly Pro Ala Ile
                 165                 170                 175 ggc ccc tgc gtg gga ggg gtc atc gtc act ttc acg agt tgg cgt gtt      576
Gly Pro Cys Val Gly Gly Val Ile Val Thr Phe Thr Ser Trp Arg Val
             180                 185                 190 atc ttc tgg ctt caa cta ggt atg agc ggg ctg ggg ctc gtg ctt tct      624
Ile Phe Trp Leu Gln Leu Gly Met Ser Gly Leu Gly Leu Val Leu Ser
             195                 200                 205 ctg cta ttt ttc ccg aaa atc gaa gga aat tct gag aag gtc tca acg      672
Leu Leu Phe Phe Pro Lys Ile Glu Gly Asn Ser Glu Lys Val Ser Thr
210                 215                 220 gcg ttt aaa ccg acc aca ctt gtc aca atc ata tcg aaa ttc tcc cca      720
Ala Phe Lys Pro Thr Thr Leu Val Thr Ile Ile Ser Lys Phe Ser Pro
225                 230                 235                 240 acg gat gtg ctc aag cag tgg gtg tat cca aat gtc ttt ctt gcc gac      768
Thr Asp Val Leu Lys Gln Trp Val Tyr Pro Asn Val Phe Leu Ala Asp
                 245                 250                 255 tta tgc tgt ggc ctc ctg gca atc acg caa tat tcg atc ctg act tca      816
Leu Cys Cys Gly Leu Leu Ala Ile Thr Gln Tyr Ser Ile Leu Thr Ser
             260                 265                 270 gct cgt gcc ata ttc aac tca cga ttt cat tta acg act gcc cta gta      864
Ala Arg Ala Ile Phe Asn Ser Arg Phe His Leu Thr Thr Ala Leu Val
             275                 280                 285 tcg ggt ctc ttc tac ctc gct cca ggt gcc ggg ttc ctg ata ggc agt      912
Ser Gly Leu Phe Tyr Leu Ala Pro Gly Ala Gly Phe Leu Ile Gly Ser
290                 295                 300 ctc gtc ggc ggt aaa ctt tcg gat cgc acc gtt cgg aga tac ata gta      960
Leu Val Gly Gly Lys Leu Ser Asp Arg Thr Val Arg Arg Tyr Ile Val
305                 310                 315                 320 aag cgc gga ttc cgt ctc cct cag gat cga ctc cac agc ggg ctc atc     1008
Lys Arg Gly Phe Arg Leu Pro Gln Asp Arg Leu His Ser Gly Leu Ile
                 325                 330                 335 aca ttg ttc gcc gtg ctg ccc gca gga acg ctc att tac ggg tgg aca     1056
Thr Leu Phe Ala Val Leu Pro Ala Gly Thr Leu Ile Tyr Gly Trp Thr
             340                 345                 350 ctc caa gag gat aag ggt gat atg gta gtg ccc ata atc gcg gcg ttc     1104
```

```
Leu Gln Glu Asp Lys Gly Asp Met Val Val Pro Ile Ile Ala Ala Phe
        355                 360                 365 ttc gcg ggc tgg ggg ctc atg ggc agt ttt aac tgc ctg aac act tac    1152
Phe Ala Gly Trp Gly Leu Met Gly Ser Phe Asn Cys Leu Asn Thr Tyr
    370                 375                 380 gtg gct ggt ttg ttc cac acc ctc att tat cta ttc cct ttg tgt aca    1200
Val Ala Gly Leu Phe His Thr Leu Ile Tyr Leu Phe Pro Leu Cys Thr
385                 390                 395                 400 tgc cca caa taa                                                    1212
Cys Pro Gln <210> SEQ ID NO 3
<211> LENGTH: 403
<212> TYPE: PRT
<213> ORGANISM: Aspergillus terreus

<400> SEQUENCE: 3

Met Gly His Gly Asp Thr Glu Ser Pro Asn Pro Thr Thr Thr Thr Glu
1               5                   10                  15

Gly Ser Gly Gln Asn Glu Pro Glu Lys Lys Gly Arg Asp Ile Pro Leu
            20                  25                  30

Trp Arg Lys Cys Val Ile Thr Phe Val Ser Trp Met Thr Leu Val
    35                  40                  45

Val Thr Phe Ser Ser Thr Cys Leu Leu Pro Ala Ala Pro Glu Ile Ala
50                  55                  60

Asn Glu Phe Asp Met Thr Val Glu Thr Ile Asn Ile Ser Asn Ala Gly
65                  70                  75                  80

Val Leu Val Ala Met Gly Tyr Ser Ser Leu Ile Trp Gly Pro Met Asn
                85                  90                  95

Lys Leu Val Gly Arg Arg Thr Ser Tyr Asn Leu Ala Ile Ser Met Leu
            100                 105                 110

Cys Ala Cys Ser Ala Gly Thr Ala Ala Ala Ile Asn Glu Glu Met Phe
        115                 120                 125

Ile Ala Phe Arg Val Leu Ser Gly Leu Thr Gly Thr Ser Phe Met Val
    130                 135                 140

Ser Gly Gln Thr Val Leu Ala Asp Ile Phe Glu Pro Val Tyr Arg Gly
145                 150                 155                 160

Thr Ala Val Gly Phe Phe Met Ala Gly Thr Leu Ser Gly Pro Ala Ile
                165                 170                 175

Gly Pro Cys Val Gly Gly Val Ile Val Thr Phe Thr Ser Trp Arg Val
            180                 185                 190

Ile Phe Trp Leu Gln Leu Gly Met Ser Gly Leu Gly Leu Val Leu Ser
        195                 200                 205

Leu Leu Phe Phe Pro Lys Ile Glu Gly Asn Ser Glu Lys Val Ser Thr
    210                 215                 220

Ala Phe Lys Pro Thr Thr Leu Val Thr Ile Ile Ser Lys Phe Ser Pro
225                 230                 235                 240

Thr Asp Val Leu Lys Gln Trp Val Tyr Pro Asn Val Phe Leu Ala Asp
                245                 250                 255

Leu Cys Cys Gly Leu Leu Ala Ile Thr Gln Tyr Ser Ile Leu Thr Ser
            260                 265                 270

Ala Arg Ala Ile Phe Asn Ser Arg Phe His Leu Thr Thr Ala Leu Val
        275                 280                 285

Ser Gly Leu Phe Tyr Leu Ala Pro Gly Ala Gly Phe Leu Ile Gly Ser
    290                 295                 300

Leu Val Gly Gly Lys Leu Ser Asp Arg Thr Val Arg Arg Tyr Ile Val
```

```
              305                 310                 315                 320
Lys Arg Gly Phe Arg Leu Pro Gln Asp Arg Leu His Ser Gly Leu Ile
                325                 330                 335
Thr Leu Phe Ala Val Leu Pro Ala Gly Thr Leu Ile Tyr Gly Trp Thr
            340                 345                 350
Leu Gln Glu Asp Lys Gly Asp Met Val Val Pro Ile Ala Ala Phe
        355                 360                 365
Phe Ala Gly Trp Gly Leu Met Gly Ser Phe Asn Cys Leu Asn Thr Tyr
    370                 375                 380
Val Ala Gly Leu Phe His Thr Leu Ile Tyr Leu Phe Pro Leu Cys Thr
385                 390                 395                 400
Cys Pro Gln

<210> SEQ ID NO 4
<211> LENGTH: 1803
<212> TYPE: DNA
<213> ORGANISM: Aspergillus oryzae

<400> SEQUENCE: 4
atgggtcaac cgatcttga atctcaaacc cccaaaacta tagacggggc cacgaaagag      60
aaggaagaga aaggcagcaa agttgaaaag ggttacggtc ttcctttgtg cggaaatgt     120 atcatcctct tcgtcgtcag ttggatgact cttgccgtta ccttctcgag cacatctctt    180
cttcctgcaa cccccgagat cgccgaggag ttcaacacca ccactgagac cctcaacatc    240
accaatgccg cgttttgct ggctatgggc ttctcgtcgc ttatctgggg tcccttgaat     300
aatctgattg aagaaggct ctcgtataac attgcgatct tcatgctctg tgtgtgttcg     360
gcagcgacgg gggctgcagt agacttgaag atgtttacgg ctttcgagt gttgagcggt    420 ttgacgggga cgtcattcat ggtatcggga cagaccattc tggcggacat ttttgaaccg    480 gtacttttc gctacctttc tctatgctcc tgtgtactag tcagttaagt actaataatg    540
gccgataggt tgtccgtggt acagccgtgg gattctttat ggctggatct gtctccggtc    600
ctgcaattgg gccctgtatc ggaggcctca tcgtcaccct tccagctgg cgcaatatct    660 actggctcca agtcggcatg acaggattcg gcctggttct agccattctc ttcgtccccg    720
aaatcaaaca ggaatccaaa gaggaacccg aagaaaaaga gaagaggaca gtactttccg    780
ccctacgcct cttcaatccc ctccgaatct tcagacaatg ggtctatccc aacgtcttct    840
tctccgtaag ccctccttcc actaactaaa actaaaccag acctcatcaa ctaacaatac    900
ctccccaaaa aggacctaac ctgcggtctc ctcgccacat tccaatactc gctcctcaca    960
tccgcccgct caatcttcaa tcccgcttc cacctcacaa cagcactcat ctccggcctc   1020
ttctacctcg ccccaggagc tggcttcctg atcggcagca tcatcggcgg caaactctcc   1080
gaccgtaccg tccgcaagta catcgtccgt cgcggcttcc gattgcccca ggatcgcctc   1140
aactccggcc tcgtcaccct gttcgccgtg ctacccgttt cggcgctgat ctacggctgg   1200
accctgcagg aggagaaggg tggtatggtc gtgccgattt tggcggcgtt ttttgcaggt   1260
tgggggctta tgggcagttt taatactttg aacacttatg ttgctggtga ttttttccat   1320
ccatccatcc atccatctat cttctttct ttctttcttt tgtttcctgt cacgtgtgca   1380
aaggcgtgga atggttgcta ataatgatac agaggctctg ccgcataagc gctccgaagt   1440
catcgctgga agtatatca tccagtatat cttttcggcg gggagtagtg cgcttgtggt   1500
gccgattatt aatgccattg gggttgggtg gacttttacc atttgtatgt ttgaccttct   1560
tcttcttctt cttcttcttc ttcttcttct tcttcttctt cttcttcttc ttcttcttct   1620
```

```
tcttcttctt cttcttcttc tttttgtttt gttacgggag gttatatgtg actgactaat    1680
tgtgtaggtg tgatcttttc catcatcggt ggtctgttaa cgatggctac cgcgcgatgg    1740
ggtctggata tgcaacaatg ggtggagagg aagttccgca ttcatgataa accagggttt    1800
tga                                                                  1803

<210> SEQ ID NO 5
<211> LENGTH: 1419
<212> TYPE: DNA
<213> ORGANISM: Aspergillus oryzae
<220> FEATURE:
<221> NAME/KEY: CDS
<222> LOCATION: (1)..(1419)

<400> SEQUENCE: 5 atg ggt caa ccc gat ctt gaa tct caa acc ccc aaa act ata gac ggg     48
Met Gly Gln Pro Asp Leu Glu Ser Gln Thr Pro Lys Thr Ile Asp Gly
1               5                   10                  15 gcc acg aaa gag aag gaa gag aaa ggc agc aaa gtt gaa aag ggt tac     96
Ala Thr Lys Glu Lys Glu Glu Lys Gly Ser Lys Val Glu Lys Gly Tyr
            20                  25                  30 ggt ctt cct ttg tgg cgg aaa tgt atc atc ctc ttc gtc gtc agt tgg    144
Gly Leu Pro Leu Trp Arg Lys Cys Ile Ile Leu Phe Val Val Ser Trp
        35                  40                  45 atg act ctt gcc gtt acc ttc tcg agc aca tct ctt cct gca acc        192
Met Thr Leu Ala Val Thr Phe Ser Ser Thr Ser Leu Leu Pro Ala Thr
    50                  55                  60 ccc gag atc gcc gag gag ttc aac acc acc act gag acc ctc aac atc    240
Pro Glu Ile Ala Glu Glu Phe Asn Thr Thr Thr Glu Thr Leu Asn Ile
65                  70                  75                  80 acc aat gcc ggc gtt ttg ctg gct atg ggc ttc tcg tcg ctt atc tgg    288
Thr Asn Ala Gly Val Leu Leu Ala Met Gly Phe Ser Ser Leu Ile Trp
                85                  90                  95 ggt ccc ttg aat aat ctg att gga aga agg ctc tcg tat aac att gcg    336
Gly Pro Leu Asn Asn Leu Ile Gly Arg Arg Leu Ser Tyr Asn Ile Ala
            100                 105                 110 atc ttc atg ctc tgt gtg tgt tcg gca gcg acg ggg gct gca gta gac    384
Ile Phe Met Leu Cys Val Cys Ser Ala Ala Thr Gly Ala Ala Val Asp
        115                 120                 125 ttg aag atg ttt acg gct ttc cga gtg ttg agc ggt ttg acg ggg acg    432
Leu Lys Met Phe Thr Ala Phe Arg Val Leu Ser Gly Leu Thr Gly Thr
    130                 135                 140 tca ttc atg gta tcg gga cag acc att ctg gcg gac att ttt gaa ccg    480
Ser Phe Met Val Ser Gly Gln Thr Ile Leu Ala Asp Ile Phe Glu Pro
145                 150                 155                 160 gtt gtc cgt ggt aca gcc gtg gga ttc ttt atg gct gga tct gtc tcc    528
Val Val Arg Gly Thr Ala Val Gly Phe Phe Met Ala Gly Ser Val Ser
                165                 170                 175 ggt cct gca att ggg ccc tgt atc gga ggc ctc atc gtc acc ttc tcc    576
Gly Pro Ala Ile Gly Pro Cys Ile Gly Gly Leu Ile Val Thr Phe Ser
            180                 185                 190 agc tgg cgc aat atc tac tgg ctc caa gtc ggc atg aca gga ttc ggc    624
Ser Trp Arg Asn Ile Tyr Trp Leu Gln Val Gly Met Thr Gly Phe Gly
        195                 200                 205 ctg gtt cta gcc att ctc ttc gtc ccc gaa atc aaa cag gaa tcc aaa    672
Leu Val Leu Ala Ile Leu Phe Val Pro Glu Ile Lys Gln Glu Ser Lys
    210                 215                 220 gag gaa ccc gaa gaa aaa gag aag agg aca gta ctt tcc gcc cta cgc    720
Glu Glu Pro Glu Glu Lys Glu Lys Arg Thr Val Leu Ser Ala Leu Arg
225                 230                 235                 240
```

```
ctc ttc aat ccc ctc cga atc ttc aga caa tgg gtc tat ccc aac gtc     768
Leu Phe Asn Pro Leu Arg Ile Phe Arg Gln Trp Val Tyr Pro Asn Val
            245                 250                 255 ttc ttc tcc gac cta acc tgc ggt ctc ctc gcc aca ttc caa tac tcg     816
Phe Phe Ser Asp Leu Thr Cys Gly Leu Leu Ala Thr Phe Gln Tyr Ser
                260                 265                 270 ctc ctc aca tcc gcc cgc tca atc ttc aat ccc cgc ttc cac ctc aca     864
Leu Leu Thr Ser Ala Arg Ser Ile Phe Asn Pro Arg Phe His Leu Thr
                275                 280                 285 aca gca ctc atc tcc ggc ctc ttc tac ctc gcc cca gga gct ggc ttc     912
Thr Ala Leu Ile Ser Gly Leu Phe Tyr Leu Ala Pro Gly Ala Gly Phe
        290                 295                 300 ctg atc ggc agc atc atc ggc ggc aaa ctc tcc gac cgt acc gtc cgc     960
Leu Ile Gly Ser Ile Ile Gly Gly Lys Leu Ser Asp Arg Thr Val Arg
305                 310                 315                 320 aag tac atc gtc cgt cgc ggc ttc cga ttg ccc cag gat cgc ctc aac    1008
Lys Tyr Ile Val Arg Arg Gly Phe Arg Leu Pro Gln Asp Arg Leu Asn
                325                 330                 335 tcc ggc ctc gtc acc ctg ttc gcc gtg cta ccc gtt tcg gcg ctg atc    1056
Ser Gly Leu Val Thr Leu Phe Ala Val Leu Pro Val Ser Ala Leu Ile
                340                 345                 350 tac ggc tgg acc ctg cag gag gag aag ggt ggt atg gtc gtg ccg att    1104
Tyr Gly Trp Thr Leu Gln Glu Glu Lys Gly Gly Met Val Val Pro Ile
            355                 360                 365 ttg gcg gcg ttt ttt gca ggt tgg ggg ctt atg ggc agt ttt aat act    1152
Leu Ala Ala Phe Phe Ala Gly Trp Gly Leu Met Gly Ser Phe Asn Thr
        370                 375                 380 ttg aac act tat gtt gct gag gct ctg ccg cat aag cgc tcc gaa gtc    1200
Leu Asn Thr Tyr Val Ala Glu Ala Leu Pro His Lys Arg Ser Glu Val
385                 390                 395                 400 atc gct gga aag tat atc atc cag tat atc ttt tcg gcg ggg agt agt    1248
Ile Ala Gly Lys Tyr Ile Ile Gln Tyr Ile Phe Ser Ala Gly Ser Ser
                405                 410                 415 gcg ctt gtg gtg ccg att att aat gcc att ggg gtt ggg tgg act ttt    1296
Ala Leu Val Val Pro Ile Ile Asn Ala Ile Gly Val Gly Trp Thr Phe
                420                 425                 430 acc att tgt gtg atc ttt tcc atc atc ggt ggt ctg tta acg atg gct    1344
Thr Ile Cys Val Ile Phe Ser Ile Ile Gly Gly Leu Leu Thr Met Ala
            435                 440                 445 acc gcg cga tgg ggt ctg gat atg caa caa tgg gtg gag agg aag ttc    1392
Thr Ala Arg Trp Gly Leu Asp Met Gln Gln Trp Val Glu Arg Lys Phe
        450                 455                 460 cgc att cat gat aaa cca ggg ttt tga                                1419
Arg Ile His Asp Lys Pro Gly Phe
465                 470

<210> SEQ ID NO 6
<211> LENGTH: 472
<212> TYPE: PRT
<213> ORGANISM: Aspergillus oryzae

<400> SEQUENCE: 6

Met Gly Gln Pro Asp Leu Glu Ser Gln Thr Pro Lys Thr Ile Asp Gly
1               5                   10                  15

Ala Thr Lys Glu Lys Glu Glu Lys Gly Ser Lys Val Glu Lys Gly Tyr
            20                  25                  30

Gly Leu Pro Leu Trp Arg Lys Cys Ile Ile Leu Phe Val Val Ser Trp
        35                  40                  45

Met Thr Leu Ala Val Thr Phe Ser Ser Thr Ser Leu Leu Pro Ala Thr
    50                  55                  60
```

Pro Glu Ile Ala Glu Glu Phe Asn Thr Thr Thr Glu Thr Leu Asn Ile
65                  70                  75                  80

Thr Asn Ala Gly Val Leu Leu Ala Met Gly Phe Ser Ser Leu Ile Trp
            85                  90                  95

Gly Pro Leu Asn Asn Leu Ile Gly Arg Arg Leu Ser Tyr Asn Ile Ala
            100                 105                 110

Ile Phe Met Leu Cys Val Cys Ser Ala Ala Thr Gly Ala Ala Val Asp
            115                 120                 125

Leu Lys Met Phe Thr Ala Phe Arg Val Leu Ser Gly Leu Thr Gly Thr
            130                 135                 140

Ser Phe Met Val Ser Gly Gln Thr Ile Leu Ala Asp Ile Phe Glu Pro
145                 150                 155                 160

Val Val Arg Gly Thr Ala Val Gly Phe Phe Met Ala Gly Ser Val Ser
            165                 170                 175

Gly Pro Ala Ile Gly Pro Cys Ile Gly Gly Leu Ile Val Thr Phe Ser
            180                 185                 190

Ser Trp Arg Asn Ile Tyr Trp Leu Gln Val Gly Met Thr Gly Phe Gly
            195                 200                 205

Leu Val Leu Ala Ile Leu Phe Val Pro Glu Ile Lys Gln Glu Ser Lys
            210                 215                 220

Glu Glu Pro Glu Glu Lys Glu Lys Arg Thr Val Leu Ser Ala Leu Arg
225                 230                 235                 240

Leu Phe Asn Pro Leu Arg Ile Phe Arg Gln Trp Val Tyr Pro Asn Val
            245                 250                 255

Phe Phe Ser Asp Leu Thr Cys Gly Leu Leu Ala Thr Phe Gln Tyr Ser
            260                 265                 270

Leu Leu Thr Ser Ala Arg Ser Ile Phe Asn Pro Arg Phe His Leu Thr
            275                 280                 285

Thr Ala Leu Ile Ser Gly Leu Phe Tyr Leu Ala Pro Gly Ala Gly Phe
            290                 295                 300

Leu Ile Gly Ser Ile Ile Gly Gly Lys Leu Ser Asp Arg Thr Val Arg
305                 310                 315                 320

Lys Tyr Ile Val Arg Arg Gly Phe Arg Leu Pro Gln Asp Arg Leu Asn
            325                 330                 335

Ser Gly Leu Val Thr Leu Phe Ala Val Leu Pro Val Ser Ala Leu Ile
            340                 345                 350

Tyr Gly Trp Thr Leu Gln Glu Glu Lys Gly Gly Met Val Val Pro Ile
            355                 360                 365

Leu Ala Ala Phe Phe Ala Gly Trp Gly Leu Met Gly Ser Phe Asn Thr
            370                 375                 380

Leu Asn Thr Tyr Val Ala Glu Ala Leu Pro His Lys Arg Ser Glu Val
385                 390                 395                 400

Ile Ala Gly Lys Tyr Ile Ile Gln Tyr Ile Phe Ser Ala Gly Ser Ser
            405                 410                 415

Ala Leu Val Val Pro Ile Ile Asn Ala Ile Gly Val Gly Trp Thr Phe
            420                 425                 430

Thr Ile Cys Val Ile Phe Ser Ile Ile Gly Gly Leu Leu Thr Met Ala
            435                 440                 445

Thr Ala Arg Trp Gly Leu Asp Met Gln Gln Trp Val Glu Arg Lys Phe
450                 455                 460

Arg Ile His Asp Lys Pro Gly Phe
465                 470

<210> SEQ ID NO 7

```
<211> LENGTH: 22
<212> TYPE: DNA
<213> ORGANISM: Artificial
<220> FEATURE:
<223> OTHER INFORMATION: primer

<400> SEQUENCE: 7
atcgtcatga ccaagcaatc tg                                                  22

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
atcgtcatga ccaagcaatc tgcggaca                                            28

<210> SEQ ID NO 9
<211> LENGTH: 28
<212> TYPE: DNA
<213> ORGANISM: Artificial
<220> FEATURE:
<223> OTHER INFORMATION: primer

<400> SEQUENCE: 9
tttagcggtg accatattcc taggccct                                            28

<210> SEQ ID NO 10
<211> LENGTH: 33
<212> TYPE: DNA
<213> ORGANISM: Artificial
<220> FEATURE:
<223> OTHER INFORMATION: primer

<400> SEQUENCE: 10
ggcattttag cggtgaccat attcctaggc ccc                                      33

<210> SEQ ID NO 11
<211> LENGTH: 1529
<212> TYPE: DNA
<213> ORGANISM: Aspergillus terreus
<220> FEATURE:
<221> NAME/KEY: CDS
<222> LOCATION: (1)..(243)
<220> FEATURE:
<221> NAME/KEY: CDS
<222> LOCATION: (300)..(1526)

<400> SEQUENCE: 11 atg acc aag caa tct gcg gac agc aac gca aag tca gga gtt acg tcc           48
Met Thr Lys Gln Ser Ala Asp Ser Asn Ala Lys Ser Gly Val Thr Ser
1               5                   10                  15 gaa ata tgt cat tgg gca tcc aac ctg gcc act gac gac atc cct tcg           96
Glu Ile Cys His Trp Ala Ser Asn Leu Ala Thr Asp Asp Ile Pro Ser
                20                  25                  30 gac gta tta gaa aga gca aaa tac ctt att ctc gac ggt att gca tgt          144
Asp Val Leu Glu Arg Ala Lys Tyr Leu Ile Leu Asp Gly Ile Ala Cys
            35                  40                  45 gcc tgg gtt ggt gca aga gtg cct tgg tca gag aag tat gtt cag gca          192
Ala Trp Val Gly Ala Arg Val Pro Trp Ser Glu Lys Tyr Val Gln Ala
        50                  55                  60 acg atg agc ttt gag ccg ccg ggg gcc tgc agg gtg att gga tat gga          240
Thr Met Ser Phe Glu Pro Pro Gly Ala Cys Arg Val Ile Gly Tyr Gly
65                  70                  75                  80
```

```
cag gtaaatttta ttcactctag acgtccaca aagtatactg acgatccttc gtatag         299
Gln aaa ctg ggg cct gtt gca gca gcc atg acc aat tcc gct ttc ata cag         347
Lys Leu Gly Pro Val Ala Ala Ala Met Thr Asn Ser Ala Phe Ile Gln
                85                  90                  95 gct acg gag ctt gac gac tac cac agc gaa gcc ccc cta cac tct gca         395
Ala Thr Glu Leu Asp Asp Tyr His Ser Glu Ala Pro Leu His Ser Ala
            100                 105                 110 agc att gtc ctt cct gcg gtc ttt gca gca agt gag gtc tta gcc gag         443
Ser Ile Val Leu Pro Ala Val Phe Ala Ala Ser Glu Val Leu Ala Glu
        115                 120                 125 cag ggc aaa aca att tcc ggt ata gat gtt att cta gcc gcc att gtg         491
Gln Gly Lys Thr Ile Ser Gly Ile Asp Val Ile Leu Ala Ala Ile Val
130                 135                 140                 145 ggg ttt gaa tct ggc cca cgg atc ggc aaa gca atc tac gga tcg gac         539
Gly Phe Glu Ser Gly Pro Arg Ile Gly Lys Ala Ile Tyr Gly Ser Asp
                    150                 155                 160 ctc ttg aac aac ggc tgg cat tgt gga gct gtg tat ggc gct cca gcc         587
Leu Leu Asn Asn Gly Trp His Cys Gly Ala Val Tyr Gly Ala Pro Ala
                165                 170                 175 ggt gcg ctg gcc aca gga aag ctc ttc ggt cta act cca gac tcc atg         635
Gly Ala Leu Ala Thr Gly Lys Leu Phe Gly Leu Thr Pro Asp Ser Met
            180                 185                 190 gaa gat gct ctc gga att gcg tgc acg caa gcc tgt ggt tta atg tcg         683
Glu Asp Ala Leu Gly Ile Ala Cys Thr Gln Ala Cys Gly Leu Met Ser
        195                 200                 205 gcg caa tac gga ggc atg gta aag cgt gtg caa cac gga ttc gca gcg         731
Ala Gln Tyr Gly Gly Met Val Lys Arg Val Gln His Gly Phe Ala Ala
210                 215                 220                 225 cgt aat ggt ctt ctt ggg gga ctg ttg gcc cat ggt ggg tac gag gca         779
Arg Asn Gly Leu Leu Gly Gly Leu Leu Ala His Gly Gly Tyr Glu Ala
                    230                 235                 240 atg aaa ggt gtc ctg gag aga tct tac ggc ggt ttc ctc aag atg ttc         827
Met Lys Gly Val Leu Glu Arg Ser Tyr Gly Gly Phe Leu Lys Met Phe
                245                 250                 255 acc aag ggc aac ggc aga gag cct ccc tac aaa gag gag gaa gtg gtg         875
Thr Lys Gly Asn Gly Arg Glu Pro Pro Tyr Lys Glu Glu Glu Val Val
            260                 265                 270 gct ggt ctc ggt tca ttc tgg cat acc ttt act att cgc atc aag ctc         923
Ala Gly Leu Gly Ser Phe Trp His Thr Phe Thr Ile Arg Ile Lys Leu
        275                 280                 285 tat gcc tgc tgc gga ctt gtc cat ggt cca gtc gag gct atc gaa aac         971
Tyr Ala Cys Cys Gly Leu Val His Gly Pro Val Glu Ala Ile Glu Asn
290                 295                 300                 305 ctt cag ggg aga tac ccc gag ctc ttg aat aga gcc aac ctc agc aac         1019
Leu Gln Gly Arg Tyr Pro Glu Leu Leu Asn Arg Ala Asn Leu Ser Asn
                    310                 315                 320 att cgc cat gtt cat gta cag ctt tca acg gct tcg aac agt cac tgt         1067
Ile Arg His Val His Val Gln Leu Ser Thr Ala Ser Asn Ser His Cys
                325                 330                 335 gga tgg ata cca gag gag aga ccc atc agt tca atc gca ggg cag atg         1115
Gly Trp Ile Pro Glu Glu Arg Pro Ile Ser Ser Ile Ala Gly Gln Met
            340                 345                 350 agt gtc gca tac att ctc gcc gtc cag ctg gtc gac cag caa tgt ctt         1163
Ser Val Ala Tyr Ile Leu Ala Val Gln Leu Val Asp Gln Gln Cys Leu
        355                 360                 365 ttg tcc cag ttt tct gag ttt gat gac aac ctg gag agg cca gaa gtt         1211
Leu Ser Gln Phe Ser Glu Phe Asp Asp Asn Leu Glu Arg Pro Glu Val
370                 375                 380                 385 tgg gat ctg gcc agg aag gtt act tca tct caa agc gaa gag ttt gat         1259
Trp Asp Leu Ala Arg Lys Val Thr Ser Ser Gln Ser Glu Glu Phe Asp
```

```
Trp Asp Leu Ala Arg Lys Val Thr Ser Ser Gln Ser Glu Glu Phe Asp
            390                 395                 400 caa gac ggc aac tgt ctc agt gcg ggt cgc gtg agg att gag ttc aac      1307
Gln Asp Gly Asn Cys Leu Ser Ala Gly Arg Val Arg Ile Glu Phe Asn
            405                 410                 415 gat ggt tct tct att acg gaa agt gtc gag aag cct ctt ggt gtc aaa      1355
Asp Gly Ser Ser Ile Thr Glu Ser Val Glu Lys Pro Leu Gly Val Lys
            420                 425                 430 gag ccc atg cca aac gaa cgg att ctc cac aaa tac cga acc ctt gct      1403
Glu Pro Met Pro Asn Glu Arg Ile Leu His Lys Tyr Arg Thr Leu Ala
            435                 440                 445 ggt agc gtg acg gac gaa tcc cgg gtg aaa gag att gag gat ctt gtc      1451
Gly Ser Val Thr Asp Glu Ser Arg Val Lys Glu Ile Glu Asp Leu Val
450                 455                 460                 465 ctc ggc ctg gac agg ctc acc gac att agc cca ttg ctg gag ctg ctg      1499
Leu Gly Leu Asp Arg Leu Thr Asp Ile Ser Pro Leu Leu Glu Leu Leu
            470                 475                 480 aat tgc ccc gta aaa tcg cca ctg gta taa                              1529
Asn Cys Pro Val Lys Ser Pro Leu Val
            485                 490

<210> SEQ ID NO 12
<211> LENGTH: 490
<212> TYPE: PRT
<213> ORGANISM: Aspergillus terreus

<400> SEQUENCE: 12

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Gly Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Phe Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala His Gly Gly Tyr Glu
225                 230                 235                 240
```

```
Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Val
            260                 265                 270

Val Ala Gly Leu Gly Ser Phe Trp His Thr Phe Thr Ile Arg Ile Lys
            275                 280                 285

Leu Tyr Ala Cys Cys Gly Leu Val His Gly Pro Val Glu Ala Ile Glu
        290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
            355                 360                 365

Leu Leu Ser Gln Phe Ser Glu Phe Asp Asp Asn Leu Glu Arg Pro Glu
        370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
            405                 410                 415

Asn Asp Gly Ser Ser Ile Thr Glu Ser Val Glu Lys Pro Leu Gly Val
            420                 425                 430

Lys Glu Pro Met Pro Asn Glu Arg Ile Leu His Lys Tyr Arg Thr Leu
            435                 440                 445

Ala Gly Ser Val Thr Asp Glu Ser Arg Val Lys Glu Ile Glu Asp Leu
        450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
            485                 490

<210> SEQ ID NO 13
<211> LENGTH: 861
<212> TYPE: DNA
<213> ORGANISM: Aspergillus terreus
<220> FEATURE:
<221> NAME/KEY: CDS
<222> LOCATION: (1)..(858)

<400> SEQUENCE: 13 atg agt att caa cat ttc cgt gtc gcc ctt att ccc ttt ttt gcg gca      48
Met Ser Ile Gln His Phe Arg Val Ala Leu Ile Pro Phe Phe Ala Ala
1               5                   10                  15 ttt tgc ctt cct gtt ttt gct cac cca gaa acg ctg gtg aaa gta aaa      96
Phe Cys Leu Pro Val Phe Ala His Pro Glu Thr Leu Val Lys Val Lys
            20                  25                  30 gat gct gaa gat cag ttg ggt gca cga gtg ggt tac atc gaa ctg gat     144
Asp Ala Glu Asp Gln Leu Gly Ala Arg Val Gly Tyr Ile Glu Leu Asp
        35                  40                  45 ctc aac agc ggt aag atc ctt gag agt ttt cgc ccc gaa gaa cgt ttt     192
Leu Asn Ser Gly Lys Ile Leu Glu Ser Phe Arg Pro Glu Glu Arg Phe
50                  55                  60 cca atg atg agc act ttt aaa gtt ctg cta tgt ggc gcg gta tta tcc     240
Pro Met Met Ser Thr Phe Lys Val Leu Leu Cys Gly Ala Val Leu Ser
65                  70                  75                  80 cgt att gac gcc ggg caa gag caa ctc ggt cgc cgc ata cac tat tct     288
```

```
cag aat gac ttg gtt gag tac tca cca gtc aca gaa aag cat ctt acg       336
Gln Asn Asp Leu Val Glu Tyr Ser Pro Val Thr Glu Lys His Leu Thr
            100                 105                 110 gat ggc atg aca gta aga gaa tta tgc agt gct gcc ata acc atg agt       384
Asp Gly Met Thr Val Arg Glu Leu Cys Ser Ala Ala Ile Thr Met Ser
        115                 120                 125 gat aac act gcg gcc aac tta ctt ctg aca acg atc gga gga ccg aag       432
Asp Asn Thr Ala Ala Asn Leu Leu Leu Thr Thr Ile Gly Gly Pro Lys
    130                 135                 140 gag cta acc gct ttt ttg cac aac atg ggg gat cat gta act cgc ctt       480
Glu Leu Thr Ala Phe Leu His Asn Met Gly Asp His Val Thr Arg Leu
145                 150                 155                 160 gat cgt tgg gaa ccg gag ctg aat gaa gcc ata cca aac gac gag cgt       528
Asp Arg Trp Glu Pro Glu Leu Asn Glu Ala Ile Pro Asn Asp Glu Arg
                165                 170                 175 gac acc acg atg cct gta gca atg gca aca acg ttg cgc aaa cta tta       576
Asp Thr Thr Met Pro Val Ala Met Ala Thr Thr Leu Arg Lys Leu Leu
            180                 185                 190 act ggc gaa cta ctt act cta gct tcc cgg caa caa tta ata gac tgg       624
Thr Gly Glu Leu Leu Thr Leu Ala Ser Arg Gln Gln Leu Ile Asp Trp
        195                 200                 205 atg gag gcg gat aaa gtt gca gga cca ctt ctg cgc tcg gcc ctt ccg       672
Met Glu Ala Asp Lys Val Ala Gly Pro Leu Leu Arg Ser Ala Leu Pro
    210                 215                 220 gct ggc tgg ttt att gct gat aaa tct gga gcc ggt gag cgt ggg tct       720
Ala Gly Trp Phe Ile Ala Asp Lys Ser Gly Ala Gly Glu Arg Gly Ser
225                 230                 235                 240 cgc ggt atc att gca gca ctg ggg cca gat ggt aag ccc tcc cgt atc       768
Arg Gly Ile Ile Ala Ala Leu Gly Pro Asp Gly Lys Pro Ser Arg Ile
                245                 250                 255 gta gtt atc tac acg acg ggg agt cag gca act atg gat gaa cga aat       816
Val Val Ile Tyr Thr Thr Gly Ser Gln Ala Thr Met Asp Glu Arg Asn
            260                 265                 270 aga cag atc gct gag ata ggt gcc tca ctg att aag cat tgg taa           861
Arg Gln Ile Ala Glu Ile Gly Ala Ser Leu Ile Lys His Trp
        275                 280                 285

<210> SEQ ID NO 14
<211> LENGTH: 286
<212> TYPE: PRT
<213> ORGANISM: Aspergillus terreus

<400> SEQUENCE: 14

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110
```

Arg Ile Asp Ala Gly Gln Glu Gln Leu Gly Arg Arg Ile His Tyr Ser
                85                  90                  95

-continued

```
Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
        130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```